US012178849B2

(12) United States Patent
Little et al.

(10) Patent No.: US 12,178,849 B2
(45) Date of Patent: *Dec. 31, 2024

(54) AUTOIMMUNE DISEASE TREATMENT WITH CHEMOKINE-LOADED ALGINATE MICROPARTICLES

(71) Applicants: UNIVERSITY OF PITTSBURGH—OF THE COMMONWEALTH SYSTEM OF HIGHER EDUCATION, Pittsburgh, PA (US); Ri.MED Foundation, Palermo (IT)

(72) Inventors: Steven R. Little, Pittsburgh, PA (US); Riccardo Gottardi, Pittsburgh, PA (US); Mintai Peter Hwang, Seoul (KR); Daniel DeSantis, Pittsburgh, PA (US)

(73) Assignees: UNIVERSITY OF PITTSBURGH—OF THE COMMONWEALTH SYSTEM OF HIGHER EDUCATION, Pittsburgh, PA (US); Ri.MED Foundation, Palermo (IT)

( * ) Notice: Subject to any disclaimer, the term of this patent is extended or adjusted under 35 U.S.C. 154(b) by 480 days.

This patent is subject to a terminal disclaimer.

(21) Appl. No.: 17/460,867

(22) Filed: Aug. 30, 2021

(65) Prior Publication Data
US 2021/0386825 A1 Dec. 16, 2021

Related U.S. Application Data

(63) Continuation of application No. 16/241,112, filed on Jan. 7, 2019, now Pat. No. 11,129,875, which is a continuation of application No. 14/418,766, filed as application No. PCT/US2013/053257 on Aug. 1, 2013, now Pat. No. 10,195,252.

(60) Provisional application No. 61/679,463, filed on Aug. 3, 2012.

(51) Int. Cl.
| | |
|---|---|
| *A61K 38/18* | (2006.01) |
| *A61K 9/127* | (2006.01) |
| *A61K 9/50* | (2006.01) |
| *A61K 35/28* | (2015.01) |
| *A61K 38/19* | (2006.01) |
| *A61K 38/30* | (2006.01) |

(52) U.S. Cl.
CPC ........ *A61K 38/1858* (2013.01); *A61K 9/1271* (2013.01); *A61K 9/5036* (2013.01); *A61K 35/28* (2013.01); *A61K 38/1841* (2013.01); *A61K 38/19* (2013.01); *A61K 38/30* (2013.01)

(58) Field of Classification Search
None
See application file for complete search history.

(56) References Cited

U.S. PATENT DOCUMENTS

| | | | |
|---|---|---|---|
| 4,717,713 A | 1/1988 | Zatz | |
| 5,364,634 A | 11/1994 | Lew | |
| 6,113,948 A | 9/2000 | Heath et al. | |
| 7,642,240 B2 | 1/2010 | Cohen | |
| 8,481,308 B2 | 7/2013 | Stern | |
| 8,728,463 B2 | 5/2014 | Atala | |
| 8,846,099 B2 | 9/2014 | Nadal Ginard | |
| 9,198,873 B2 | 12/2015 | Hsieh | |
| 9,572,795 B2 | 2/2017 | Hossainy | |
| 9,855,370 B2 | 1/2018 | Breuer | |
| 2004/0248796 A1 | 12/2004 | Alitalo | |
| 2007/0081976 A1 | 4/2007 | Cohen | |
| 2008/0254019 A1 | 10/2008 | Kato | |
| 2011/0008443 A1 | 1/2011 | Alsberg | |
| 2011/0300203 A1* | 12/2011 | Mao ........................ | A61P 19/02 435/395 |
| 2013/0337076 A1 | 12/2013 | Brakenhielm | |

FOREIGN PATENT DOCUMENTS

EP    2 322 147 A1    6/2011

OTHER PUBLICATIONS

U.S. Appl. No. 14/418,766 (U.S. Pat. No. 10,195,252), filed Jan. 30, 2015 (Feb. 5, 2019).
U.S. Appl. No. 16/241,112 (U.S. Pat. No. 11,129,875), filed Jan. 7, 2019 (Sep. 28, 2021).
U.S. Appl. No. 14/418,766, Dec. 18, 2018 Issue Fee Payment.
U.S. Appl. No. 14/418,766, Sep. 21, 2018 Notice of Allowance.
U.S. Appl. No. 14/418,766, Aug. 9, 2018 Amendment and Request for Continued Examination (RCE).
U.S. Appl. No. 14/418,766, May 9, 2018 Final Office Action.
U.S. Appl. No. 14/418,766, Feb. 1, 2018 Response to Non-Final Office Action.
U.S. Appl. No. 14/418,766, Aug. 1, 2017 Non-Final Office Action.
U.S. Appl. No. 14/418,766, May 12, 2017 Amendment and Request for Continued Examination (RCE).
U.S. Appl. No. 14/418,766, Jan. 17, 2017 Final Office Action.
U.S. Appl. No. 14/418,766, Oct. 21, 2016 Response to Non-Final Office Action.
U.S. Appl. No. 14/418,766, May 31, 2016 Non-Final Office Action.
U.S. Appl. No. 14/418,766, May 20, 2016 Response to Restriction Requirement.

(Continued)

*Primary Examiner* — Daniel C Gamett
(74) *Attorney, Agent, or Firm* — Baker Botts L.L.P.

(57) ABSTRACT

The present invention provides microparticles that induce the migration of multipotent stem cells to the anatomical site of the microparticles. Various release profiles are demonstrated that depend upon the relative concentration of alginate in the chemokine-loaded microparticle. Local administration and/or intraarticular injection of the microparticles are useful in conditions such as osteoarthritis. Targeted systemic delivery of the alginate chemokine microparticles to distant anatomical sites subjected to autoimmune disease symptomology can be performed by encapsulation within liposomes having targeting ligands. Consequently, upon the creation of the appropriate chemokine gradient, multipotent stem cells will migrate to the distant anatomical site where the liposomes are attached.

12 Claims, 15 Drawing Sheets

(56) References Cited

OTHER PUBLICATIONS

U.S. Appl. No. 14/418,766, Feb. 22, 2016 Restriction Requirement.
U.S. Appl. No. 16/241,112, Aug. 26, 2021 Issue Fee Payment.
U.S. Appl. No. 16/241,112, Jun. 7, 2021 Notice of Allowance.
U.S. Appl. No. 16/241,112, May 26, 2021 Notice of Allowance.
U.S. Appl. No. 16/241,112, Apr. 8, 2021 Response to Non-Final Office Action.
U.S. Appl. No. 16/241,112, Jan. 29, 2021 Non-Final Office Action.
U.S. Appl. No. 16/241,112, Jan. 8, 2021 Response to Restriction Requirement.
U.S. Appl. No. 16/241,112, Dec. 1, 2020 Restriction Requirement.
Al-Refu, "Stem Cells and Alopecia: a Review of Pathogenesis." Br J Dermatol, 167(3):479-484 (2012).
Azarnia et al., J Microencapsul. Feb. 2008;25(1):46-58 (Abstract only).
Bai, et al., "Human Bone Marrow-Derived Mesenchymal Stem Cells Induce Th2-Polarized Immune Response and Promote Endogenous Repair in Animal Models of Multiple Sclerosis." Glia, 57(11):1192-1203 (2009).
Barrilleaux, et al., "Review: Ex Vivo Engineering of Living Tissues with Adult Stem Cells." Tissue Eng, 12(11):3007-3019 (2006).
Bernardo, "Human Mesenchymal Stromal Cells: Biological Characterization and Clinical Application." Doctoral thesis, Leiden University. Publisher: Department of Immunohematology and Blood Transfusion, Faculty of Medicine /Leiden University Medical Center (LUMC), Leiden University. Chapters 1-7; pp. 9-259 (2010).
Bernardo, et al., "Phenotypical/Functional Characterization of in Vitro-Expanded Mesenchymal Stromal Cells from Patients with Crohn's Disease." Cytotherapy, 11(7):825-836 (2009).
Bouffi, et al., "Multipotent Mesenchymal Stromal Cells and Rheumatoid Arthritis: Risk or Benefit?" Rheumatology (Oxford), 48(10):1185-1189 (2009).
Campagnoli, et al., "Identification of Mesenchymal Stem/Progenitor Cells in Human First-Trimester Fetal Blood, Liver, and Bone Marrow." Blood, 98(8):2396-2402 (2001).
Caplan, "Adult Mesenchymal Stem Cells for Tissue Engineering Versus Regenerative Medicine." J Cell Physiol, 213(2):341-347 (2007).
Caplan, "Mesenchymal Stem Cells: The Past, the Present, the Future." Cartilage, 1(1):6-9 (2010).
Caplan, "Review: Mesenchymal Stem Cells: Cell-Based Reconstructive Therapy in Orthopedics." Tissue Eng, 11(7-8):1198-1211 (2005).
Carpenter-Green and Huang, "Incorporation of Acylated Wheat Germ Agglutinin into Liposomes." Anal Biochem, 135(1):151-155 (1983).
Casalini, et al., "Tumor Pretargeting: Role of Avidin/Streptavidin on Monoclonal Antibody Internalization." J Nucl Med, 38(9):1378-1381 (1997).
Chan, et al., "Mhc Expression Kinetics and Immunogenicity of Mesenchymal Stromal Cells after Short-Term Ifn-Gamma Challenge." Exp Hematol, 36(11):1545-1555 (2008).
Chanvillard, et al., "The Role of Natural Killer Cells in Multiple Sclerosis and Their Therapeutic Implications." Front Immunol, 4:63 (2013).
Chua, et al., "Attachment of Immunoglobulin to Liposomal Membrane Via Protein Carbohydrate." Biochim Biophys Acta, 800(3):291-300 (1984).
Constantin, et al., "Adipose-Derived Mesenchymal Stem Cells Ameliorate Chronic Experimental Autoimmune Encephalomyelitis." Stem Cells, 27(10):2624-2635 (2009).
Cramp, et al., "Health Behaviour Change Interventions for the Promotion of Physical Activity in Rheumatoid Arthritis: a Systematic Review." Musculoskeletal Care, 11(4):238-247 (2013).
Crosasso, et al., "Antitumoral Activity of Liposomes and Immunoliposomes Containing 5-Fluorouridine Prodrugs." J Pharm Sci, 86(7):832-839 (1997).

De Bari, et al., "Multipotent Mesenchymal Stem Cells from Adult Human Synovial Membrane." Arthritis Rheum, 44(8):1928-1942 (2001).
De La Riva, et al., "Local controlled release of VEGF and PDGF from a combined brushite-chitosan system enhances bone regeneration." Journal of Controlled Release, 143:45—52 (2010).
De La Riva, et al., "VEGF-controlled release within a bone defect from alginate/chitosan/PLA-H scaffolds." European Journal of Pharmaceutics and Biopharmaceutics, '73(1): 50-58 (2009).
Derksen and Scherphof "An Improved Method for the Covalent Coupling of Proteins to Liposomes." Biochimica et Biophysica Acta (BBA)—Biomembranes, 814(1):151-155 (1985).
Di Nicola, et al., "Human Bone Marrow Stromal Cells Suppress T-Lymphocyte Proliferation Induced by Cellular or Nonspecific Mitogenic Stimuli." Blood, 99(10):3838-3843 (2002).
Ding, et al., "Mesenchymal Stem Cells Prevent the Rejection of Fully Allogenic Islet Grafts by the Immunosuppressive Activity of Matrix Metalloproteinase-2 and -9." Diabetes, 58(8):1797-1806 (2009).
Erices, et al., "Mesenchymal Progenitor Cells in Human Umbilical Cord Blood." Br J Haematol, 109(1):235-242 (2000).
Fan, et al., "Characterization and Neural Differentiation of Fetal Lung Mesenchymal Stem Cells." Cell Transplant, 14(5):311-321 (2005).
Fiorina, et al., "Immunomodulatory Function of Bone Marrow-Derived Mesenchymal Stem Cells in Experimental Autoimmune Type 1 Diabetes." J Immunol, 183(2):993-1004 (2009).
Giordano and Sinha "Cytokine Pathways and Interactions in Alopecia Areata." Eur J Dermatol, 23(3):308-318 (2013).
Gonzalez, et al., "Adipose-Derived Mesenchymal Stem Cells Alleviate Experimental Colitis by Inhibiting Inflammatory and Autoimmune Responses." Gastroenterology, 136(3):978-989 (2009).
Gonzalez-Rey, et al., "Human Adult Stem Cells Derived from Adipose Tissue Protect against Experimental Colitis and Sepsis." Gut, 58(7):929-939 (2009).
Goren, et al., "Targeting of Stealth Liposomes to Erbb-2 (Her/2) Receptor: In Vitro and in Vivo Studies." Br J Cancer, 74(11):1749-1756 (1996).
Groh, et al., "Human Mesenchymal Stem Cells Require Monocyte-Mediated Activation to Suppress Alloreactive T Cells." Exp Hematol, 33(8):928-934 (2005).
Gronthos, et al., "Postnatal Human Dental Pulp Stem Cells (Dpscs) in Vitro and in Vivo." Proceedings of the National Academy of Sciences, 97(25):13625-13630 (2000).
Hansen, et al., "Attachment of Antibodies to Sterically Stabilized Liposomes: Evaluation, Comparison and Optimization of Coupling Procedures." Biochimica et Biophysica Acta (BBA)—Biomembranes, 1239(2):133-144 (1995).
Hao et al., Cardiovasc Res. Jul. 1, 2007;75(1):178-185.
Harding, et al., "Immunogenicity and Pharmacokinetic Attributes of Poly(Ethylene Glycol)-Grafted Immunoliposomes." Biochim Biophys Acta, 1327(2):181-192 (1997).
Harsch, et al., "Targeting of Monoclonal Antibody-Coated Liposomes to Sheep Red Blood Cells." Biochem Biophys Res Commun, 103(3):1069-1076 (1981).
Hayashi, et al., "Topical Implantation of Mesenchymal Stem Cells Has Beneficial Effects on Healing of Experimental Colitis in Rats." J Pharmacol Exp Ther, 326(2):523-531 (2008).
Holzer, et al., "Successful Autologous Stem Cell Transplantation in Two Patients with Juvenile Dermatomyositis." Scand J Rheumatol, 39(1):88-92 (2010).
Horwitz, et al., "Isolated Allogeneic Bone Marrow-Derived Mesenchymal Cells Engraft and Stimulate Growth in Children with Osteogenesis Imperfecta: Implications for Cell Therapy of Bone." Proc Natl Acad Sci USA, 99(13):8932-8937 (2002).
Huang, et al., "Monoclonal Antibody Covalently Coupled with Fatty Acid. A Reagent for in Vitro Liposome Targeting." J Biol Chem, 255(17):8015-8018 (1980).
Hughes and Khamashta, "Seronegative Antiphospholipid Syndrome." Ann Rheum Dis, 62(12):1127 (2003).
Hughes, et al., "Monoclonal Antibody Targeting of Liposomes to Mouse Lung in Vivo." Cancer Res, 49(22):6214-6220 (1989).

(56) References Cited

OTHER PUBLICATIONS

In 't Anker, et al., "Amniotic Fluid as a Novel Source of Mesenchymal Stem Cells for Therapeutic Transplantation." Blood, 102(4):1548-1549 (2003).
Ishida, et al., "Liposomes Bearing Polyethyleneglycol-Coupled Transferrin with Intracellular Targeting Property to the Solid Tumors in Vivo." Pharm Res, 18(7):1042-1048 (2001).
Iso, et al., "Multipotent Human Stromal Cells Improve Cardiac Function after Myocardial Infarction in Mice without Long-Term Engraftment." Biochem Biophys Res Commun, 354(3):700-706 (2007).
Jay et al., Biomaterials, Apr. 2010;31(11):3054-3062 (Year: 2010).
Jay et al., J Control Release. Feb. 20, 2009;134(1):26-34 (Year: 2009).
Jay et al., J Control Release. FASEB J.Aug. 2008; 22(8): 2949-2956 (Year: 2008).
Kang, et al., "Interactions between Human Adipose Stromal Cells and Mouse Neural Stem Cells in Vitro." Brain Res Dev Brain Res, 145(1):141-149 (2003).
Kim, et al., "Immunotherapeutic Treatment of Autoimmune Diabetes." Crit Rev Immunol, 33(3):245-281 (2013).
Kirpotin, et al., "Sterically Stabilized Anti-Her2 Immunoliposomes: Design and Targeting to Human Breast Cancer Cells in Vitro." Biochemistry, 36(1):66-75 (1997).
Kohler and Milstein, "Continuous Cultures of Fused Cells Secreting Antibody of Predefined Specificity." Nature, 256(5517):495-497 (1975).
Koning, et al., "Efficient Intracellular Delivery of 5-Fluorodeoxyuridine into Colon Cancer Cells by Targeted Immunoliposomes." Cancer Detect Prev, 26(4):299-307 (2002).
Kuznetsov, et al., "Circulating Skeletal Stem Cells." J Cell Biol, 153(5):1133-1140 (2001).
Lanz, et al., "Mouse Mesenchymal Stem Cells Suppress Antigen-Specific Th Cell Immunity Independent of Indoleamine 2,3-Dioxygenase 1 (Idol)." Stem Cells Dev, 19(5):657-668 (2010).
Lee, et al., "Multipotent Stromal Cells from Human Marrow Home to and Promote Repair of Pancreatic Islets and Renal Glomeruli in Diabetic Nod/Scid Mice." Proc Natl Acad Sci USA, 103(46):17438-17443 (2006).
Lopes de Menezes, et al., "In Vitro and in Vivo Targeting of Immunoliposomal Doxorubicin to Human B-Cell Lymphoma." Cancer Res, 58(15):3320-3330 (1998).
Loughrey, et al., "A Non-Covalent Method of Attaching Antibodies to Liposomes." Biochim Biophys Acta, 901(1):157-160 (1987).
Ma and Liu, "Micrornas in the Pathogenesis of Systemic Lupus Erythematosus." International Journal of Rheumatic Diseases, 16(2):115-121 (2013).
MacFarlane, et al., "Anti-Inflammatory Role and Immunomodulation of Mesenchymal Stem Cells in Systemic Joint Diseases: Potential for Treatment." Expert Opin Ther Targets, 17(3):243-254 (2013).
Magnani et al., "Quantitative comparison of direct antibody labeling and tumor pretargeting in uveal melanoma" J Nucleic Med 37:967-971 (1996).
Majumdar, et al., "Characterization and Functionality of Cell Surface Molecules on Human Mesenchymal Stem Cells." J Biomed Sci, 10(2):228-241 (2003).
Mao "Biotinylation of Antibodies." Methods Mol Biol, 588:49-52 (2010).
Marcuzzi, et al., "Genetic and Functional Profiling of Crohn's Disease: Autophagy Mechanism and Susceptibility to Infectious Diseases." Biomed Res Int, 2013:297501 (2013).
Maruyama, et al., "Targetability of Novel Immunoliposomes Modified with Amphipathic Poly(Ethylene Glycol)S Conjugated at Their Distal Terminals to Monoclonal Antibodies." Biochim Biophys Acta, 1234(1):74-80 (1995).
Miao, et al., "The Emerging Role of Micrornas in the Pathogenesis of Systemic Lupus Erythematosus." Cellular Signalling, 25(9):1828-1836 (2013).
Millar "Molecular Mechanisms Regulating Hair Follicle Development." J Invest Dermatol, 118(2):216-225 (2002).
Miller, et al., "Degradation Rates of Oral Resorbable Implants (Polylactates and Polyglycolates): Rate Modification with Changes in PLA/PGA Copolymer Ratios." J Biomed Mater Res, 11(5):711-719 (1977).
Moro, et al., "Tumor Cell Targeting with Antibody-Avidin Complexes and Biotinylated Tumor Necrosis Factor Alpha." Cancer Res, 57(10):1922-1928 (1997).
Najafi, et al., "Autoimmunity in Inflammatory Bowel Disease: a Case of Ulcerative Colitis with Diabetes Mellitus, Autoimmune Hepatitis and Autoimmune Hypothyroidism." Turk J Pediatr, 54(6):651-653 (2012).
Nayfe, et al., "Seronegative Antiphospholipid Syndrome." Rheumatology (Oxford), 52(8):1358-1367 (2013).
Nobs, et al., "Current Methods for Attaching Targeting Ligands to Liposomes and Nanoparticles." J Pharm Sci, 93(8):1980-1992 (2004).
Noort, et al., "Mesenchymal Stem Cells Promote Engraftment of Human Umbilical Cord Blood-Derived CD34(+) Cells in Nod/Scid Mice." Exp Hematol, 30(8):870-878 (2002).
Ortiz, et al., "Mesenchymal Stem Cell Engraftment in Lung is Enhanced in Response to Bleomycin Exposure and Ameliorates Its Fibrotic Effects." Proc Natl Acad Sci USA, 100(14):8407-8411 (2003).
Otsuka, et al., "Multipotent Hemopoietic Progenitor Cells in Patients with Systemic Lupus Erythematosus." J Rheumatol, 15(7):1085-1090 (1988).
Parekkadan, et al., "Bone Marrow-Derived Mesenchymal Stem Cells Ameliorate Autoimmune Enteropathy Independently of Regulatory T Cells." Stem Cells, 26(7):1913-1919 (2008).
Park, et al., "Anti-Her2 Immunoliposomes for Targeted Therapy of Human Tumors." Cancer Lett, 118(2):153-160 (1997).
Park, et al., "Anti-Her2 Immunoliposomes: Enhanced Efficacy Attributable to Targeted Delivery." Clin Cancer Res, 8(4):1172-1181 (2002).
Phinney and Prockop, "Concise Review: Mesenchymal Stem/Multipotent Stromal Cells: The State of Transdifferentiation and Modes of Tissue Repair—Current Views." Stem Cells, 25(11):2896-2902 (2007).
Phinney, et al., "Biological Activities Encoded by the Murine Mesenchymal Stem Cell Transcriptome Provide a Basis for Their Developmental Potential and Broad Therapeutic Efficacy." Stem Cells, 24(1):186-198 (2006).
Pieri and Barritault, "Biotinylated Basic Fibroblast Growth Factor is Biologically Active." Anal Biochem, 195(2):214-219 (1991).
Portnoy, et al., "Monoclonal Antibody-Based Assay for Alt Al, a Major Alternaria Allergen." Ann Allergy Asthma Immunol, 81(1):59-64 (1998).
Prockop ""Sternness" Does Not Explain the Repair of Many Tissues by Mesenchymal Stem/Multipotent Stromal Cells (Mscs)." Clin Pharmacol Ther, 82(3):241-243 (2007).
Putney and Burke, "Improving Protein Therapeutics with Sustained-Release Formulations." Nat Biotechnol, 16(2):153-157 (1998).
Rafei, et al., "Allogeneic Mesenchymal Stem Cells for Treatment of Experimental Autoimmune Encephalomyelitis." Mol Ther, 17(10):1799-1803 (2009).
Rasmusson, et al., "Mesenchymal Stem Cells Inhibit the Formation of Cytotoxic T Lymphocytes, but Not Activated Cytotoxic T Lymphocytes or Natural Killer Cells." Transplantation, 76(8):1208-1213 (2003).
Rice and Scolding, "Adult Human Mesenchymal Cells Proliferate and Migrate in Response to Chemokines Expressed in Demyelination." Cell Adh Migr, 4(2):235-240 (2010).
Schena, et al., "Interferon-Gamma-Dependent Inhibition of B Cell Activation by Bone Marrow-Derived Mesenchymal Stem Cells in a Murine Model of Systemic Lupus Erythematosus." Arthritis Rheum, 62(9):2776-2786 (2010).
Shen, et al., "An Improved Method for Covalent Attachment of Antibody to Liposomes." Biochim Biophys Acta, 689(1):31-37 (1982).
Signore, et al., "Identity and Ranking of Colonic Mesenchymal Stromal Cells." J Cell Physiol, 227(9):3291-3300 (2012).

(56) References Cited

OTHER PUBLICATIONS

Singer and Caplan, "Mesenchymal Stem Cells: Mechanisms of Inflammation." Annu Rev Pathol, 6:457-478 (2011).
Statkute, et al., "Antiphospholipid Syndrome in Patients with Systemic Lupus Erythematosus Treated by Autologous Hematopoietic Stem Cell Transplantation." Blood, 106(8):2700-2709 (2005).
Tanaka, et al., "Exogenous Administration of Mesenchymal Stem Cells Ameliorates Dextran Sulfate Sodium-Induced Colitis Via Anti-Inflammatory Action in Damaged Tissue in Rats." Life Sci, 83(23-24):771-779 (2008).
Tilakaratne et al., Biomaterials. Jan. 2007;28(1):89-98.
Torchilin, et al., "Incorporation of Hydrophilic Protein Modified with Hydrophobic Agent into Liposome Membrane." Biochim Biophys Acta, 602(3):511-521 (1980).
Torchilin, et al., "Phosphatidylinositol May Serve as the Hydrophobic Anchor for Immobilization of Proteins on Liposome Surface." FEBS Letters, 138(1):117-120 (1982).
Tremain, et al., "Microsage Analysis of 2,353 Expressed Genes in a Single Cell-Derived Colony of Undifferentiated Human Mesenchymal Stem Cells Reveals Mrnas of Multiple Cell Lineages." Stem Cells, 19(5):408-418 (2001).
Tyndall and Uccelli, "Multipotent Mesenchymal Stromal Cells for Autoimmune Diseases: Teaching New Dogs Old Tricks." Bone Marrow Transplant, 43(11):821-828 (2009).
Van den Hoven et al., Mol Pharm. Aug. 1, 2011;8(4):1002-1015.
Vinh and Behr, "Crohn's as an Immune Deficiency: From Apparent Paradox to Evolving Paradigm." Expert Rev Clin Immunol, 9(1):17-30 (2013).
Vulcan, et al., "Dendritic Cells as a Major Source of Macrophage-Derived Chemokine/CCL22 in Vitro and in Vivo." Eur J Immunol, 31(3):812-822 (2001).
Wang, et al., "Efficacy of Allogeneic Mesenchymal Stem Cell Transplantation in Patients with Drug-Resistant Polymyositis and Dermatomyositis." Ann Rheum Dis, 70(7):1285-1288 (2011).
Weissig, et al., "A New Hydrophobic Anchor for the Attachment of Proteins to Liposomal Membranes." FEBS Lett, 202(1):86-90 (1986).
Welter, et al., "Simplification of Aggregate Culture of Human Mesenchymal Stem Cells as a Chondrogenic Screening Assay." Biotechniques, 42(6):732, 734-737 (2007).
Williams, et al., "Cells Isolated from Adult Human Skeletal Muscle Capable of Differentiating into Multiple Mesodermal Phenotypes." Am Surg, 65(1):22-26 (1999).
Wu, et al., "CCL22 Is Involved in the Recruitment of CD4+CD25 High T Cells into Tuberculous Pleural Effusions." Respirology, 15(3):522-529 (2010).
Xu, et al., "Allogeneic Mesenchymal Stem Cell Treatment Alleviates Experimental and Clinical Sjogren Syndrome." Blood, 120(15):3142-3151 (2012).
Xu, et al., "IL-32 with Potential Insights into Rheumatoid Arthritis." Clin Immunol, 147(2):89-94 (2013).
Yang, et al., "Evaluation of Bone Marrow-and Brain-Derived Neural Stem Cells in Therapy of Central Nervous System Autoimmunity." Am J Pathol, 177(4):1989-2001 (2010).
Yao, et al., "A Role for the Endothelium in Vascular Calcification." Circ Res, 113(5):495-504 (2013).
Young et al., "Mesenchymal Stem Cells Resude within the Connective Tissues of Many Organs." Dev Dyn, 202(2):137-144 (1995).
Zappia, et al., "Mesenchymal Stem Cells Ameliorate Experimental Autoimmune Encephalomyelitis Inducing T-Cell Anergy." Blood, 106(5):1755-1761 (2005).
Zhao, et al., "Human Mesenchymal Stromal Cells Ameliorate the Phenotype of SOD1-G93A ALS Mice." Cytotherapy, 9(5):414-426 (2007).
Ziv, et al., "The Plastic Pancreas." Dev Cell, 26(1):3-7 (2013).
Zuk, et al., "Multilineage Cells from Human Adipose Tissue: Implications for Cell-Based Therapies." Tissue Eng, 7(2):211-228 (2001).

\* cited by examiner

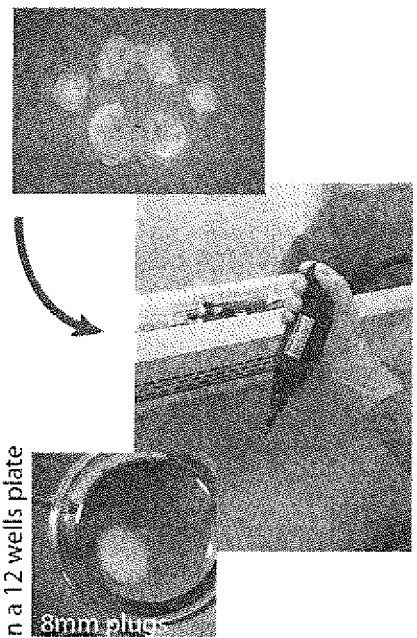
Fig. 8A
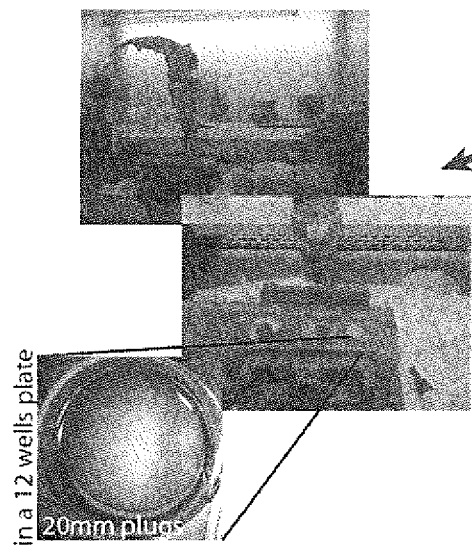
Fig. 8B
Fig. 8C

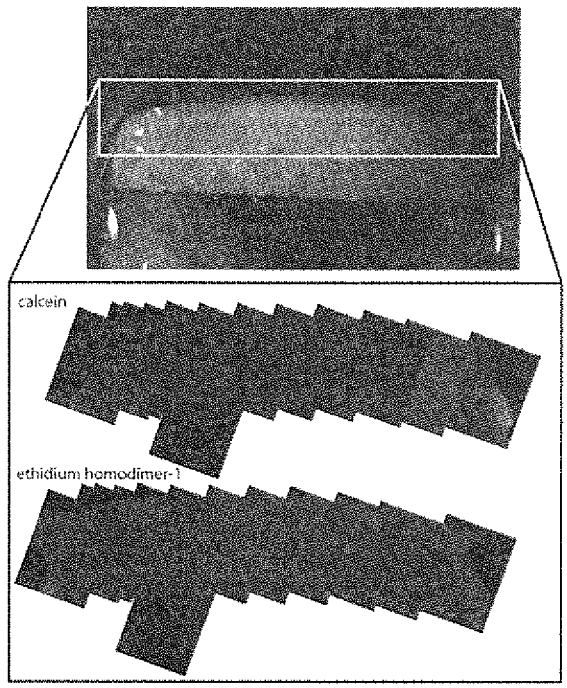
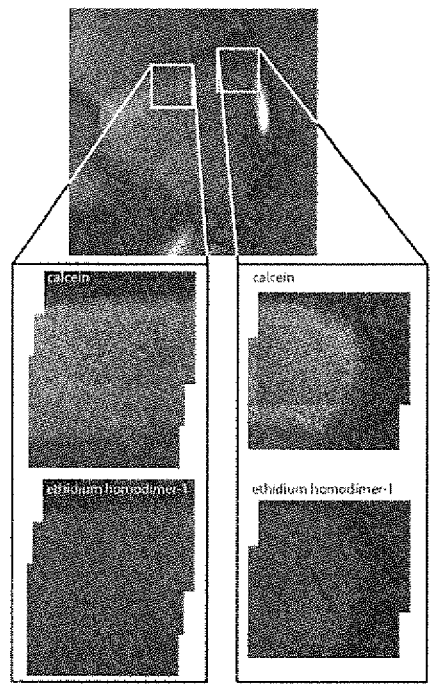
Fig. 9A
Fig. 9B

AUTOIMMUNE DISEASE TREATMENT WITH CHEMOKINE-LOADED ALGINATE MICROPARTICLES

CROSS-REFERENCE TO RELATED APPLICATION

This application is a continuation application of U.S. patent application Ser. No. 16/241,112 (now allowed), filed Jan. 7, 2019, which is a continuation application of U.S. patent application Ser. No. 14/418,766 (now issued as U.S. Pat. No. 10,195,252), filed Jan. 30, 2015, which is a National Stage Entry of International Patent Application No. PCT/US2013/053257, filed on Aug. 1, 2013, which claims priority to U.S. Provisional Application No. 61/679,463, filed on Aug. 3, 2012, the contents of each of which are incorporated by reference in their entireties, and to each of which priority is claimed.

FIELD OF THE INVENTION

The present invention is related to compositions and methods for inducing the migration of multipotent stem cells. For example, a controlled release microparticle may be configured to release at least one chemokine under conditions such that a biomimetic chemokine gradient is created. This biomimetic chemokine gradient induces the migration of multipotent stem cells to the anatomical location of the microparticles. Variations in alginate concentration of microparticles alters chemokine release kinetics and profile and may be useful in inducing the migration of specific subsets of multipotent stem cells.

BACKGROUND

Autoimmune diseases arise from an inappropriate immune response of the body against substances and tissues normally present in the body (autoimmunity). This may be restricted to certain organs (e.g. in autoimmune thyroiditis) or involve a particular tissue in different places (e.g. Goodpasture's disease which may affect the basement membrane in both the lung and the kidney). The treatment of autoimmune diseases is typically with immunosuppression—medication that decreases the immune response. A large number of autoimmune diseases are recognized. A substantial minority of the population suffers from these diseases, which are often chronic, debilitating, and life-threatening. There are more than eighty illnesses caused by autoimmunity. It has been estimated that autoimmune diseases are among the ten leading causes of death among women in all age groups up to 65 years.

In both autoimmune and inflammatory diseases the condition arises through aberrant reactions of the human adaptive or innate immune systems. In autoimmunity, the patient's immune system is activated against the body's own proteins. In inflammatory diseases, it is the overreaction of the immune system, and its subsequent downstream signaling which causes problems. Mitigation of inflammation by activation of anti-inflammatory genes and the suppression of inflammatory genes in immune cells have been suggested as possible therapies.

What is needed in the art is a personalized therapy approach to treating autoimmune diseases that is mediated by the patient's immune system.

SUMMARY OF THE INVENTION

The present invention is related to compositions and methods for inducing the migration of multipotent stem cells. For example, a controlled release microparticle may be configured to release at least one chemokine under conditions such that a biomimetic chemokine gradient is created. This biomimetic chemokine gradient induces the migration of multipotent stem cells to the anatomical location of the microparticles. Variations in alginate concentration of microparticles alters chemokine release kinetics and profile and may be useful in inducing the migration of specific subsets of multipotent stem cells.

A composition comprising a controlled release microparticle, wherein said microparticle comprises at least one chemokine, wherein the microparticle is configured to provide a chemokine release profile over a forty day period. In one embodiment, the chemokine release profile is predicted. In one embodiment the microparticle comprises alginate. In one embodiment, the alginate concentration ranges between approximately 1-4%. In one embodiment, the predicted chemokine release profile is trimodal. In one embodiment, the predicted chemokine release profile is bimodal. In one embodiment, the predicted chemokine release profile is exponential. In one embodiment, the predicted chemokine release profile is linear. In one embodiment, the chemokine includes, but is not limited to, TGFα, PDGF, IGFs, CXCL12, CCL5, and/or CCL22.

A composition comprising a controlled release alginate microparticle, wherein said microparticle comprises at least one chemokine, wherein the microparticle is configured to provide a chemokine release profile over a forty day period. In one embodiment, the chemokine release profile is predicted. In one embodiment, the alginate concentration ranges between approximately 1-4%. In one embodiment, the predicted chemokine release profile is trimodal. In one embodiment, the predicted chemokine release profile is bimodal. In one embodiment, the predicted chemokine release profile is exponential. In one embodiment, the predicted chemokine release profile is linear. In one embodiment, the chemokine includes, but is not limited to, TGFα, PDGF, IGFs, CXCL12, CCL5, and/or CCL22.

A composition comprising a controlled release alginate microparticle, wherein said microparticle comprises approximately 1% alginate, at least one chemokine, and is configured to provide a trimodal release profile of the at least one chemokine over a forty day period. In one embodiment, the trimodal chemokine release profile comprises a linear phase. In one embodiment, the linear phase occurs during days 1-15 of the forty day period. In one embodiment, the trimodal chemokine release profile comprises an exponential phase. In one embodiment, the exponential phase occurs during days 16-20 of the forty day period. In one embodiment, the trimodal chemokine release profile comprises a non-release phase. In one embodiment, the non-release phase occurs during days 21-40 of the forty day period. In one embodiment, the chemokine includes, but is not limited to, TGFα, PDGF, IGFs, CXCL12, CCL5, and/or CCL22.

A composition comprising a controlled release alginate microparticle, wherein said microparticle comprises approximately 1.5% alginate, at least one chemokine and is configured to provide a bimodal release profile of the at least one chemokine over a forty day period. In one embodiment, the bimodal chemokine release profile comprises a first linear phase. In one embodiment, the first linear phase occurs during days 1-20 of the forty day period. In one embodiment, the bimodal chemokine release profile comprises a second linear phase, wherein the release rate of the second linear phase is less than the release rate of the first linear phase. In one embodiment, the second linear phase occurs during days 21-40 of the forty day period. In one embodiment, the chemokine includes, but is not limited to, TGFα, PDGF, IGFs, CXCL12, CCL5, and/or CCL22.

A composition comprising a controlled release alginate microparticle, wherein said microparticle comprises approximately 2% alginate, at least one chemokine, and is configured to provide a trimodal release profile of the at least one chemokine over a 40 day period. In one embodiment, the trimodal chemokine release profile comprises a first linear phase. In one embodiment, the first linear phase occurs during day 1-6 of the forty day period. In one embodiment, the trimodal chemokine release profile comprises a non-release phase. In one embodiment, the non-release phase occurs during day 7-16 of the forty day period. In one embodiment, the trimodal chemokine release profile comprises a second linear phase, wherein the release rate of the second linear phase is less than the release rate of the first linear phase. In one embodiment, the second linear phase occurs between day 17-40 of the forty day period. In one embodiment, the chemokine includes, but is not limited to, TGFα, PDGF, IGFs, CXCL12, CCL5, and/or CCL22.

A composition comprising a controlled release alginate microparticle, wherein said microparticle comprises approximately 3% alginate, at least one chemokine, and is configured to provide an exponential release profile of the at least one chemokine. In one embodiment, the exponential chemokine release profile comprises an exponential release phase. In one embodiment, the exponential release phase occurs between day 8-12 of the forty day period. In one embodiment, the chemokine includes, but is not limited to, TGFα, PDGF, IGFs, CXCL12, CCL5, and/or CCL22.

A composition comprising a controlled release alginate microparticle, wherein said microparticle comprises approximately 4% alginate, at least one chemokine and is configured to provide a linear release profile of the at least one chemokine. In one embodiment, the linear chemokine release profile comprises a zero order release phase. In one embodiment, the zero order release phase occurs during day 1-40 of the forty day period. In one embodiment, the chemokine includes, but is not limited to, TGFα, PDGF, IGFs, CXCL12, CCL5, and/or CCL22.

A method comprising: a) providing; i) a composition comprising a controlled release microparticle comprising at least one chemokine, wherein the microparticle is configured to provide a predicted release profile of the at least one chemokine; ii) a plurality of multipotent stem cells within a patient exhibiting at least one symptom of a disease; and b) administering the composition to the patient under conditions such that a chemokine gradient is created wherein the at least one symptom of the disease is reduced. In one embodiment, the microparticle comprises alginate. In one embodiment, the alginate is in a concentration ranging between approximately 1-4%. In one embodiment, the method further comprises the step of inducing a migration of the multipotent stem cells by the chemokine gradient. In one embodiment, the migration of the multipotent stem cells is towards the microparticles. In one embodiment, the chemokine includes, but is not limited to, TGFα, PDGF, IGFs, CXCL12, CCL5, and/or CCL22.

A method comprising: a) providing; i) a composition comprising a controlled release alginate microparticle comprising at least one chemokine, wherein the microparticle is configured to provide a predicted release profile of the at least one chemokine; ii) a plurality of multipotent stem cells within a patient exhibiting at least one symptom of a disease; and b) administering the composition to the patient under conditions such that a chemokine gradient is created wherein the at least one symptom of the disease is reduced. In one embodiment, the method further comprises the step of inducing a migration of the multipotent stem cells by the chemokine gradient. In one embodiment, the migration of the multipotent stem cells is towards the microparticles. In one embodiment, the chemokine includes, but is not limited to, TGFα, PDGF, IGFs, CXCL12, CCL5, and/or CCL22. In one embodiment, the administering is intraarticular. In one embodiment, the composition comprises a liposome, wherein the liposome comprises at least one targeting ligand. In one embodiment, the targeting ligand has specific affinity for an anatomical site. In one embodiment, the anatomical site comprises an organ. In one embodiment, the anatomical site comprises a tissue. In one embodiment, the administering is parenteral. In one embodiment, the microparticle comprises 1% alginate wherein the predicted chemokine release profile comprises a linear phase and an exponential phase. In one embodiment, the microparticle comprises 1.5% alginate wherein the predicted chemokine release profile comprises a first linear phase and a second linear phase, wherein the release rate of the second linear phase is slower than the release rate of the first linear phase. In one embodiment, the microparticle comprises 2% alginate wherein the predicted chemokine release profile comprises a first linear phase, a non-release phase and a second linear phase, wherein the release rate of the second linear phase is slower than the release rate of the first linear phase. In one embodiment, the microparticle comprises 3% alginate wherein the predicted chemokine release profile comprises an exponential phase. In one embodiment, the microparticle comprises 4% alginate wherein the predicted chemokine release profile comprises a linear phase. In one embodiment, the at least one symptom of said disease includes, but is not limited to, local inflammation, tissue degeneration, tissue damage, lack of wound healing and dysregulated homeostasis. In one embodiment, the disease is osteoarthritis. In one embodiment, the disease is an autoimmune disease. In one embodiment, the autoimmune disease includes, but is not limited to, Type 1 diabetes, alopecia areata, systemic lupus erythematosus, Sjogren syndrome, rheumatoid arthritis, antiphospholipid antibody syndrome, multiple sclerosis, Crohn's disease, ulcerative colitis, and/or dermatomyositis.

A method comprising: a) providing: i) a composition comprising a controlled release alginate microparticle comprising at least one chemokine, wherein the microparticle is configured to provide a predicted release profile of the at least one chemokine; ii) a plurality of multipotent stem cells within a patient exhibiting at least one symptom of osteoarthritis; and b) administering the composition to the patient under conditions such that a chemokine gradient is created wherein the at least one symptom of osteoarthritis is reduced. In one embodiment, the method further comprises the step of inducing a migration of the multipotent stem cells by the chemokine gradient. In one embodiment, the migration of the multipotent stem cells is towards the microparticles. In one embodiment, the chemokine includes, but is not limited to, TGFα, PDGF, IGFs, CXCL12, CCL5, and/or CCL22. In one embodiment, the administering includes, but is not limited to, intraarticular, parenteral, topical, local, patches and/or oral. In one embodiment, the microparticle comprises 3% alginate wherein the predicted chemokine release profile comprises an exponential phase. In one embodiment, the microparticle comprises 4% alginate wherein the predicted chemokine release profile comprises a linear phase.

A use for a composition comprising a controlled release alginate microparticle comprising at least one chemokine, wherein the microparticle is configured to provide a predicted release profile of the at least one chemokine in the preparation of a medicament to create a chemokine gradient in a patient comprising a plurality of multipotent stem cells and exhibiting at least one symptom of a disease. In one embodiment, the disease is an autoimmune disease. In one embodiment, the autoimmune disease includes, but is not limited to, Type 1 diabetes, alopecia areata, systemic lupus erythematosus, Sjogren syndrome, rheumatoid arthritis, antiphospholipid antibody syndrome, multiple sclerosis, Crohn's disease, ulcerative colitis, and/or dermatomyositis. In one embodiment, the concentration of alginate in said microparticle is selected from at least one of the group consisting of 1%, 1.5%, 2%, 3% and 4%. In one embodiment the predicted release profile is selected from at least one of the group consisting of linear, bimodal, trimodal and exponential. In one embodiment, the chemokine includes, but is not limited to, TGFα, PDGF, IGFs, CXCL12, CCL5, and/or CCL22.

A use for a composition comprising a controlled release alginate microparticle comprising at least one chemokine, wherein the microparticle is configured to provide a predicted release profile of the at least one chemokine in the preparation of a medicament to create a chemokine gradient in a patient comprising a plurality of multipotent stem cells and exhibiting at least one symptom of osteoarthritis. In one embodiment, the concentration of alginate in the microparticle is 3% and the predicted release profile is exponential. In one embodiment, the concentration of alginate in the microparticle is 4% and the predicted release profile is linear. In one embodiment, the chemokine includes, but is not limited to, TGFα, PDGF, IGFs, CXCL12, CCL5, and/or CCL22.

Definitions

The term, "multipotent stem cell", "mesenchymal stem cell, or "multipotent stromal cell" refer to any undifferentiated cell that can differentiate into a variety of cell types, including, but not limited to, osteoblasts (bone cells) and chondrocytes (cartilage cells), and possess both a regenerative and regulatory potential.

The term, "chemokine" as used herein, refers to any compound belonging to a group of chemotactic cytokines that are produced by various cells, that are thought to provide directional cues for the movement of circulating biological cells (i.e., for example, multipotent stem cells, white blood cells, T cells, monocytes, and/or neutrophils). For example, a chemokine may include, but is not limited to, platelet derived growth factor (PDGF), Transforming growth factor alpha (TGFα), insulin-like growth factor (IGF), stromal cell-derived factor 1 (SDF-1) also known as C—X—C motif chemokine 12 (CXCL12), Chemokine (C—C motif) ligand 5 (CCL5 or RANTES), and C—C motif chemokine 22 (CCL22).

The term, "cytokine" as used herein, refers to any compound belonging to a group of immunoregulatory proteins (i.e., for example, interleukins (IL), tumor necrosis factors (TNF), and/or interferons (IF)) that are usually secreted by immunological cells. For example, a cytokine may include, but is not limited to, IL-1, IL-2, IL-12, IL-32, TNFα and/or IFβ.

The term "suspected of having", as used herein, refers a medical condition or set of medical conditions (e.g., preliminary symptoms) exhibited by a patient that is insufficient to provide a differential diagnosis. Nonetheless, the exhibited condition(s) would justify further testing (e.g., autoantibody testing) to obtain further information on which to base a diagnosis.

The term "at risk for" as used herein, refers to a medical condition or set of medical conditions (e.g., risk factors) exhibited by a patient which may predispose the patient to a particular disease or affliction. For example, these conditions may result from influences that include, but are not limited to, behavioral, emotional, chemical, biochemical, or environmental influences.

The term "effective amount" as used herein, refers to a particular amount of a pharmaceutical composition comprising a therapeutic compound that achieves a clinically beneficial result (i.e., for example, a reduction of symptoms). Toxicity and therapeutic efficacy of such compositions can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, and it can be expressed as the ratio $LD_{50}/ED_{50}$. Compounds that exhibit large therapeutic indices are preferred. The data obtained from these cell culture assays and additional animal studies can be used in formulating a range of dosage for human use. The dosage of such compounds lies preferably within a range of circulating concentrations that include the $ED_{50}$ with little or no toxicity. The dosage varies within this range depending upon the dosage form employed, sensitivity of the patient, and the route of administration.

The term "symptom", as used herein, refers to any subjective or objective evidence of disease or physical disturbance observed by the patient. For example, subjective evidence is usually based upon patient self-reporting and may include, but is not limited to, pain, headache, visual disturbances, nausea and/or vomiting. Alternatively, objective evidence is usually a result of medical testing including, but not limited to, body temperature, complete blood count, lipid panels, thyroid panels, blood pressure, heart rate, electrocardiogram, tissue and/or body imaging scans.

The term "disease" or "medical condition", as used herein, refers to any impairment of the normal state of the living animal or plant body or one of its parts that interrupts or modifies the performance of the vital functions. Typically manifested by distinguishing signs and symptoms, it is usually a response to: i) environmental factors (as malnutrition, industrial hazards, or climate); ii) specific infective agents (as worms, bacteria, or viruses); iii) inherent defects of the organism (as genetic anomalies); and/or iv) combinations of these factors.

The terms "reduce," "inhibit," "diminish," "suppress," "decrease," "prevent" and grammatical equivalents (including "lower," "smaller," etc.) when in reference to the expression of any symptom in an untreated subject relative to a treated subject, mean that the quantity and/or magnitude of the symptoms in the treated subject is lower than in the untreated subject by any amount that is recognized as clinically relevant by any medically trained personnel. In one embodiment, the quantity and/or magnitude of the symptoms in the treated subject is at least 10% lower than, at least 25% lower than, at least 50% lower than, at least 75% lower than, and/or at least 90% lower than the quantity and/or magnitude of the symptoms in the untreated subject.

The term "administered" or "administering", as used herein, refers to any method of providing a composition to a patient such that the composition has its intended effect on the patient. An exemplary method of administering is by a direct mechanism such as, local tissue administration (i.e., for example, extravascular placement), intraarticular injection, parenteral injection, oral ingestion, transdermal patch, topical, inhalation, suppository etc.

The term "patient" or "subject", as used herein, is a human or animal and need not be hospitalized. For example, out-patients, persons in nursing homes are "patients." A patient may comprise any age of a human or non-human animal and therefore includes both adult and juveniles (i.e., children). It is not intended that the term "patient" connote a need for medical treatment, therefore, a patient may voluntarily or involuntarily be part of experimentation whether clinical or in support of basic science studies.

The term "affinity" as used herein, refers to any attractive force between substances or particles that causes them to enter into and remain in chemical combination. For example, an inhibitor compound that has a high affinity for a receptor will provide greater efficacy in preventing the receptor from interacting with its natural ligands, than an inhibitor with a low affinity.

The term "derived from" as used herein, refers to the source of a compound or sequence. In one respect, a compound or sequence may be derived from an organism or particular species. In another respect, a compound or sequence may be derived from a larger complex or sequence.

The term "protein" as used herein, refers to any of numerous naturally occurring extremely complex substances (as an enzyme or antibody) that consist of amino acid residues joined by peptide bonds, contain the elements carbon, hydrogen, nitrogen, oxygen, usually sulfur. In general, a protein comprises amino acids having an order of magnitude within the hundreds.

The term "peptide" as used herein, refers to any of various amides that are derived from two or more amino acids by combination of the amino group of one acid with the carboxyl group of another and are usually obtained by partial hydrolysis of proteins. In general, a peptide comprises amino acids having an order of magnitude with the tens.

The term "polypeptide", refers to any of various amides that are derived from two or more amino acids by combination of the amino group of one acid with the carboxyl group of another and are usually obtained by partial hydrolysis of proteins. In general, a peptide comprises amino acids having an order of magnitude with the tens or larger.

The term "pharmaceutically" or "pharmacologically acceptable", as used herein, refer to molecular entities and compositions that do not produce adverse, allergic, or other untoward reactions when administered to an animal or a human.

The term, "pharmaceutically acceptable carrier", as used herein, includes any and all solvents, or a dispersion medium including, but not limited to, water, ethanol, polyol (for example, glycerol, propylene glycol, and liquid polyethylene glycol, and the like), suitable mixtures thereof, and vegetable oils, coatings, isotonic and absorption delaying agents, liposome, commercially available cleansers, and the like. Supplementary bioactive ingredients also can be incorporated into such carriers.

The term, "purified" or "isolated", as used herein, may refer to a peptide composition that has been subjected to treatment (i.e., for example, fractionation) to remove various other components, and which composition substantially retains its expressed biological activity.

Where the term "substantially purified" is used, this designation will refer to a composition in which the protein or peptide forms the major component of the composition, such as constituting about 50%, about 60%, about 70%, about 80%, about 90%, about 95% or more of the composition (i.e., for example, weight/weight and/or weight/volume). The term "purified to homogeneity" is used to include compositions that have been purified to "apparent homogeneity" such that there is single protein species (i.e., for example, based upon SDS-PAGE or HPLC analysis). A purified composition is not intended to mean that some trace impurities may remain.

As used herein, the term "substantially purified" refers to molecules, either nucleic or amino acid sequences, that are removed from their natural environment, isolated or separated, and are at least 60% free, preferably 75% free, and more preferably 90% free from other components with which they are naturally associated. An "isolated polynucleotide" is therefore a substantially purified polynucleotide.

The terms "amino acid sequence" and "polypeptide sequence" as used herein, are interchangeable and to refer to a sequence of amino acids.

As used herein the term "portion" when in reference to a protein (as in "a portion of a given protein") refers to fragments of that protein. The fragments may range in size from four amino acid residues to the entire amino acid sequence minus one amino acid.

The term "antibody" refers to immunoglobulin evoked in animals by an immunogen (antigen). It is desired that the antibody demonstrates specificity to epitopes contained in the immunogen. The term "polyclonal antibody" refers to immunoglobulin produced from more than a single clone of plasma cells; in contrast "monoclonal antibody" refers to immunoglobulin produced from a single clone of plasma cells.

The terms "specific binding" or "specifically binding" when used in reference to the interaction of an antibody and a protein or peptide means that the interaction is dependent upon the presence of a particular structure (i.e., for example, an antigenic determinant or epitope) on a protein; in other words an antibody is recognizing and binding to a specific protein structure rather than to proteins in general. For example, if an antibody is specific for epitope "A", the presence of a protein containing epitope A (or free, unlabeled A) in a reaction containing labeled "A" and the antibody will reduce the amount of labeled A bound to the antibody.

The term "small organic molecule" as used herein, refers to any molecule of a size comparable to those organic molecules generally used in pharmaceuticals. The term excludes biological macromolecules (e.g., proteins, nucleic acids, etc.). Preferred small organic molecules range in size from approximately 10 Da up to about 5000 Da, more preferably up to 2000 Da, and most preferably up to about 1000 Da.

The term "sample" as used herein is used in its broadest sense and includes environmental and biological samples. Environmental samples include material from the environment such as soil and water. Biological samples may be animal, including, human, fluid (e.g., blood, plasma and serum), solid (e.g., stool), tissue, liquid foods (e.g., milk), and solid foods (e.g., vegetables). For example, a pulmonary sample may be collected by bronchoalveolar lavage (BAL) which comprises fluid and cells derived from lung tissues. A biological sample may include, but is not limited to, a cell, tissue extract, and/or body fluid.

The term "derivative" as used herein, refers to any chemical modification of a nucleic acid or an amino acid. Illustrative of such modifications would be replacement of hydrogen by an alkyl, acyl, or amino group. For example, a nucleic acid derivative would encode a polypeptide which retains essential biological characteristics.

The term "biologically active" refers to any molecule having structural, regulatory or biochemical functions. For example, biological activity may be determined, for example, by restoration of wild-type growth in cells lacking protein activity. Cells lacking protein activity may be produced by many methods (i.e., for example, point mutation and frame-shift mutation). Complementation is achieved by transfecting cells which lack protein activity with an expression vector which expresses the protein, a derivative thereof, or a portion thereof.

The term "immunologically active" defines the capability of a natural, recombinant or synthetic peptide, or any oligopeptide thereof, to induce a specific immune response in appropriate animals or cells and/or to bind with specific antibodies.

The term "antigenic determinant" as used herein refers to that portion of a molecule that is recognized by a particular antibody (i.e., an epitope). When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The terms "immunogen," "antigen," "immunogenic" and "antigenic" refer to any substance capable of generating antibodies when introduced into an animal. By definition, an immunogen must contain at least one epitope (the specific biochemical unit capable of causing an immune response), and generally contains many more. Proteins are most frequently used as immunogens, but lipid and nucleic acid moieties complexed with proteins may also act as immunogens. The latter complexes are often useful when smaller molecules with few epitopes do not stimulate a satisfactory immune response by themselves.

The term "antibody" refers to immunoglobulin evoked in animals by an immunogen (antigen). It is desired that the antibody demonstrates specificity to epitopes contained in the immunogen. The term "polyclonal antibody" refers to immunoglobulin produced from more than a single clone of plasma cells; in contrast "monoclonal antibody" refers to immunoglobulin produced from a single clone of plasma cells.

The terms "homology" and "homologous" as used herein in reference to amino acid sequences refer to the degree of identity of the primary structure between two amino acid sequences. Such a degree of identity may be directed a portion of each amino acid sequence, or to the entire length of the amino acid sequence. Two or more amino acid sequences that are "substantially homologous" may have at least 50% identity, preferably at least 75% identity, more preferably at least 85% identity, most preferably at least 95%, or 100% identity.

The terms "binding component", "molecule of interest", "agent of interest", "targeting ligand" or "receptor" as used herein may be any of a large number of different molecules, biological cells or aggregates, and the terms are used interchangeably. Each binding component may be immobilized on a solid substrate and binds to an analyte being detected. Proteins, polypeptides, peptides, nucleic acids (nucleotides, oligonucleotides and polynucleotides), antibodies, ligands, saccharides, polysaccharides, microorganisms such as bacteria, fungi and viruses, receptors, antibiotics, test compounds (particularly those produced by combinatorial chemistry), plant and animal cells, organdies or fractions of each and other biological entities may each be a binding component.

The term "bind" as used herein, includes any physical attachment or close association, which may be permanent or temporary. Generally, an interaction of hydrogen bonding, hydrophobic forces, van der Waals forces, covalent and ionic bonding etc., facilitates physical attachment between the molecule of interest and the analyte being measuring.

BRIEF DESCRIPTION OF THE FIGURES

FIG. 1A: PDGF release profile with a 1% alginate microparticle.

FIG. 1B: PDGF release profile with a 1.5% alginate microparticle.

FIG. 1C: PDGF release profile with a 2% alginate microparticle.

FIG. 1D: PDGF release profile with a 3% alginate microparticle.

FIG. 1E: PDGF release profile with a 4% alginate microparticle.

FIG. 4A: Basic experimental design of an injured articular joint mouse model where luciferin-labeled MSCs and alginate PDGF microparticles are injected into a mouse given an intra-articular joint mono-iodoacetate injection.

FIG. 4B: Lack of destruction of articular cartilage following a blank microparticle population injection.

FIG. 4C: Showing how luciferin-labeled MSCs should migrate to the articular joint injected with mono-iodoacetate (see fluorescent spots on the left leg of each mouse)

FIG. 5A: Representative articular cartilage after a PBS injection.

FIG. 5B: Representative articular cartilage three (3) days after a blank alginate microparticle injection.

FIG. 5C: Representative articular cartilage twenty-one (21) days after blank alginate microparticle injection.

FIG. 6A: Shows rounded, smooth surfaced microparticles immediately after release begins.

FIG. 6B: A close up view of a microparticle of FIG. 6A.

FIG. 6C: Shows irregular, rough surfaced microparticles thirty (30) days after release.

FIG. 6D: A close up view of a microparticle of FIG. 6C.

FIG. 7A: Bright field image of the microparticle/MSC mixture.

FIG. 7B: Calcein staining (green) of the microparticles/MSC mixture to show viable MSCs.

FIG. 7C: Ethidum heterodimer-1 staining (red) of the microparticle/MSC mixture to show non-viable MSCs.

FIG. 7D: Overlay of FIGS. 7A-7C.

FIGS. 8A-8C illustrates how different sized osteochondral plugs (e.g., 8-20 mm) are obtained from arthroplasty samples by using different drill sizes.

FIG. 8A: Various embodiments of arthroplasty samples.

FIG. 8B: Production of 20 mm osteochondral plugs.

FIG. 8C: Production of 8 mm osteochondral plugs.

FIGS. 9A and 9B present exemplary data showing improved bone cell viability during osteochondral plug drilling using a live/dead cell protocol. Live Cells (green): calcein. Dead Cells (red): ethidium homodimer-1.

FIG. 9A: Massive cell death after using conventional drilling techniques.

FIG. 9B: Little or no cell death after drilling was performed during cold saline irrigation.

DETAILED DESCRIPTION OF THE INVENTION

Figure 1A:
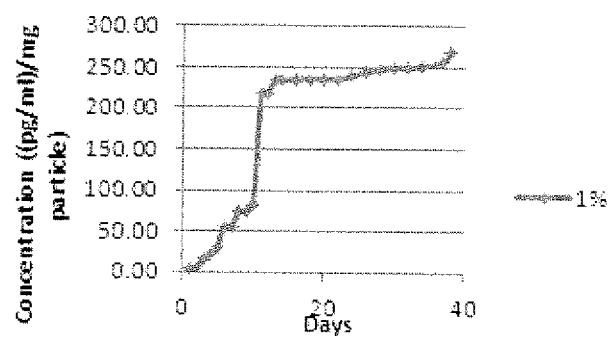
FIGS. 1A-1E provide exemplary data of PDGF from microparticles comprising different alginate formulations using cumulative release profiles.

The present invention is related to compositions and methods for inducing the migration of multipotent stem cells. For example, a controlled release microparticle may be configured to release at least one chemokine under conditions such that a biomimetic chemokine gradient is created. This biomimetic chemokine gradient induces the migration of multipotent stem cells to the anatomical location of the microparticles. Variations in alginate concentration of microparticles alters chemokine release kinetics and profile and may be useful in inducing the migration of specific subsets of multipotent stem cells.

I. Multipotent Stem Cells

Multipotent stem cells (MSCs), also referred to in the art as mesenchymal stem cells, are derived from multipotent stromal cells that can differentiate into a variety of cell types, including osteoblasts (bone cells) and chondrocytes (cartilage cells), and possess both a regenerative and regulatory potential. MSCs can promote tissue repair and growth, which may follow, for instance, exercise or damage. They generally interact via contact, cytokines, and lyposomes secretion, with nearby cells to modulate cell response. Among MSCs regulatory role, particularly notable is their immunosuppressive and anti-inflammatory potential and the capacity to regulate cells of the immune system. Furthermore, during inflammation or local tissue damage, and even during development, different molecules are locally released by the body and operate as chemokines to naturally attract MSCs. Among these are, for instance, interleukins, Transforming growth factor alpha, PDGF, IGFs, CXCL12, CCL5, CCL22, of which PDGF has been recognized to be the most effective in inducing MSCs migration.

Chemokines are a family of small cytokines, or signaling proteins secreted by cells. Their name is derived from their ability to induce directed chemotaxis in nearby responsive cells; they are chemotactic cytokines. Proteins are classified as chemokines according to shared structural characteristics such as small size (they are all approximately 8-10 kilodaltons in size), and the presence of four cysteine residues in conserved locations that are key to forming their 3-dimensional shape. However, these proteins have historically been known under several other names including the SIS family of cytokines, SIG family of cytokines, SCY family of cytokines, Platelet factor-4 superfamily or intercrines. Some chemokines are considered homeostatic and are involved in controlling the migration of cells during normal processes of tissue maintenance or development. Chemokines are found in all vertebrates, some viruses and some bacteria, but none have been described for other invertebrates.

Chemokines have been classified into at least four main subfamilies: CXC, CC, CX3C and XC. All of these proteins exert their biological effects by interacting with G protein-linked transmembrane receptors called chemokine receptors, that are selectively found on the surfaces of their target cells. The major role of chemokines is to act as a chemoattractant to guide the migration of cells. Cells that are attracted by chemokines follow a signal of increasing chemokine concentration towards the source of the chemokine. Some chemokines have roles in development; they promote angiogenesis (the growth of new blood vessels), or guide cells to tissues that provide specific signals critical for cellular maturation.

The main function of chemokines is to manage the migration of leukocytes (homing) in the respective anatomical locations in inflammatory and homeostatic processes. Homeostatic chemokines are produced in the thymus and lymphoid tissues. Their homeostatic function in homing is best exemplified by the chemokines CCL19 and CCL21 (expressed within lymph nodes and on lymphatic endothelial cells) and their receptor CCR7 (expressed on cells destined for homing in cells to these organs). Among other homeostatic chemokine receptors include: CCR9, CCR10, and CXCR5, which are a part of the cell addresses for tissue-specific homing of leukocytes. CCR9 supports the migration of leukocytes into the intestine, CCR 10 to the skin and CXCR5 supports the migration of B-cell to follicles of lymph nodes. As well CXCL12 (SDF-1) constitutively produced in the bone marrow promotes proliferation of progenitor B cells in the bone marrow microenvironment.

Platelet derived growth factor (PDGF) is expected to induce MSC migration in vivo because it has been shown to be involved in the regulation of cell growth and division. In particular, PDGF plays a role in blood vessel formation (angiogenesis), the growth of blood vessels from already-existing blood vessel tissue. In chemical terms, platelet-derived growth factor is a dimeric glycoprotein composed of two A (-AA) or two B (-BB) chains or a combination of the two (-AB). PDGF is a potent mitogen for cells of mesenchymal origin, including smooth muscle cells and glial cells. In both mouse and human, the PDGF signaling network consists of four ligands, PDGFA-D, and two receptors, PDGFR(alpha) and PDGFR(beta). All PDGFs function as secreted, disulphide-linked homodimers, but only PDGFA and B can form functional heterodimers. Though it is synthesized, stored and released by platelets upon activation, it is produced by a plethora of cells including smooth muscle cells, activated macrophages, and endothelial cells.

Transforming growth factor alpha (TGFα) is expected to induce MSC migration in vivo because it is produced in macrophages, brain cells, and keratinocytes, and induces epithelial development. It is closely related to epithelial growth factor (EGF), and can also bind to the EGF receptor with similar effects. TGFα stimulates neural cell proliferation in the adult injured brain. TGFα was cited in the 2001 NIH Stem Cell report to the U.S. Congress as promising evidence for the ability of adult stem cells to restore function in neurodegenerative disorders.

Insulin-like growth factor (IGF) is expected to induce MSC migration in vivo because it has been shown to be involved in the promotion of cell proliferation and the inhibition of cell death (apoptosis). Insulin-like growth factor 2 (IGF-2) is thought to be a primary growth factor required for early development while IGF-1 expression is required for achieving maximal growth. IGF-I has an involvement in regulating neural development including neurogenesis, myelination, synaptogenesis, and dendritic branching and neuroprotection after neuronal damage.

Stromal cell-derived factor 1 (SDF-1) also known as C—X—C motif chemokine 12 (CXCL12) is expected to induce MSC migration in vivo because it has been shown to be involved in leukocyte activation and are often induced by proinflammatory stimuli such as lipopolysaccharide, TNF, or ILI. CXCL12 is strongly chemotactic for lymphocytes. During embryogenesis it directs the migration of hematopoietic cells from foetal liver to bone marrow and the formation of large blood vessels. Mice that were knocked-out for CXCL12 gene were lethal before the birth or within just 1 hour of life. In adulthood, CXCL12 plays an important role in angiogenesis by recruiting endothelial progenitor cells (EPCs) from the bone marrow through a CXCR4 dependent mechanism Chemokine (C—C motif) ligand 5 (CCL5 or RANTES) is expected to induce MSC migration in vivo because it has been shown to be involved in inducing chemotaxis for T cells, eosinophils, and basophils, and plays an active role in recruiting leukocytes into inflammatory sites. With the help of particular cytokines (i.e., IL-2 and IFN-γ) that are released by T cells, CCL5 also induces the proliferation and activation of certain natural-killer (NK) cells to form CHAK (CC-Chemokine-activated killer) cells.

C—C motif chemokine 22 (CCL22) is expected to induce MSC migration in vivo because it has been shown to elicit its effects on its target cells by interacting with cell surface chemokine receptors such as CCR4. Vulcano et al., "Dendritic cells as a major source of macrophage-derived chemokine/CCL22 in vitro and in vivo" *Eur. J Immunol.* 31(3): 812-822 (2001); and Wu et al., "CCL22 is involved in the recruitment of CD4+CD25 high T cells into tuberculous pleural effusions" *Respirology* 15(3):522-529 (2010).

Adult human mesenchymal stem cells (hMSCs) can be isolated from a variety of tissues, including, but not limited to, bone marrow, muscle, fat, and/or dermis. In particular, MSCs or MSC-like cells have been elaborated from skeletal muscle (Williams et al., "Cells isolated from adult human skeletal muscle capable of differentiating into multiple mesodermal phenotypes" Am Surg 65:22-26 (1999)), adipose tissue (Zuk et al., "Multilineage cells from human adipose tissue: Implications for cell-based therapies" *Tissue Eng* 7:211-228 (2001)); umbilical cord (Erices et al., "Mesenchymal progenitor cells in human umbilical cord blood" *Br J Haematol* 109:235-242 (2000)): synovium (De Bari et al., "Multipotent mesenchymal stem cells from adult human synovial membrane" *Arthritis Rheum* 44:1928-1942 (2001)), the circulatory system (Kuznetsov et al., "Circulating skeletal stem cells" *J Cell Biol* 153:1133-1140 (2001)), dental pulp (Gronthos et al., "Postnatal human dental pulp stem cells (DPSCs) in vitro and in vivo" *Proc Nail Acad Sci USA* 97:13625-13630 (2000)), amniotic fluid (In't Anker et al., "Amniotic fluid as a novel source of mesenchymal stem cells for therapeutic transplantation" *Blood* 102:1548-1549 (2003)); as well as fetal blood, liver, bone marrow, and lung (Noort et al., "Mesenchymal stem cells promote engraftment of human umbilical cord blood-derived CD34(+) cells in NOD/SCID mice" *Exp Hematol* 30:870-878 (2002); Campagnoli et al., "Identification of mesenchymal stem/progenitor cells in human first-trimester fetal blood, liver, and bone marrow" *Blood* 98:2396-3402 (2001); and Fan et al., "Characterization and neural differentiation of fetal lung mesenchymal stem cells" *Cell Transplant* 14:311-321 (2005). Therefore, it appears that MSCs reside within the connective tissue of most organs as predicted by early studies with chick embryos. Young et al., "Mesenchymal stem cells reside within the connective tissues of many organs" *Dev Dyn* 202:137-144 (1995).

Depending on the stimulus and the culture conditions employed, these cells can form tissues including, but not limited to, bone, cartilage, muscle, fat, and other connective tissues. These observations originally suggested that MSCs were responsible for the normal turnover and maintenance of adult mesenchymal tissues, but over the past decade it has become clear that all MSCs are pericytes and that it is their pleiotropic nature that allows them to sense and respond to an event in the local environment, be it injury or inflammation. Caplan A I., "Adult mesenchymal stem cells for tissue engineering versus regenerative medicine" *J. Cell Physiol.* 213:341-347 (2007); Caplan A I., "Mesenchymal stem cells" *J. Orthop. Res.* 9:641-650 (1991); and Caplan A I., "Review: mesenchymal stem cells: cell-based reconstructive therapy in orthopedics" *Tissue Eng.* 11:1198-1211 (2005).

In general, it is accepted in the art that cells isolated from adult bone marrow and are multipotent for skeletal phenotype are referred to as hMSCs because their reparative function appears to extend beyond the integumentary and musculoskeletal system. Unlike HSCs, hMSCs can be culture expanded ex vivo in up to 40 to 50 cell doublings without differentiation. Welter et al., "Simplification of aggregate culture of human mesenchymal stem cells as a chondrogenic screening assay" *Biotechniques* 42:732-737 (2007). In vitro, MSCs can be activated in order to suppress T cell proliferation. MSC effects on T cell proliferation in vitro appear to have both contact-dependent and contact-independent components. Groh et al., "Human mesenchymal stem cells require monocyte mediated activation to suppress alloreactive T cells" *Exp. Hematol.* 33:928-934 (2005). This conclusion resulted from observations that conditioned medium from MSCs activated either singly or in combination with cytokines (IL-1β) tumor necrosis factor α (TNF-α), and/or interferon-γ (IFN-γ)). However, IL-1β may not require combinations of cytokines and may alone be sufficient to prime hMSCs, whereas the effect of IFN-γ may be amplified in the presence of other proinflammatory cytokines, such as IL-1β and TNF-α. Theoretically, IFN-γ may also interfere with hMSC function. One of the reasons that hMSCs appear to be immune privileged is that constitutively freshly isolated and cultured MSCs lack MHC class II expression. In the presence of IFN-γ, culture may induce MHC class II expression and transform MSCs into cells that can act as APCs rather than as immune-modulating cells. Chan et al., "MHC expression kinetics and immunogenicity of mesenchymal stromal cells after short-term IFN-γ challenge" *Exp. Hematol.* 36:1545-55 (2008).

Consistent with results from in vitro studies, murine allogeneic MSCs are effective in the treatment of murine models of human disease. Fiorina et al., "Immunomodulatory function of bone marrow-derived mesenchymal stem cells in experimental autoimmune type 1 diabetes" *J. Immunol.* 183:993-1004 (2009); Parekkadan et al., "Bone marrow-derived mesenchymal stem cells ameliorate autoimmune enteropathy independently of regulatory T cells" *Stem Cells* 26:1913-1919 (2008). Several studies have documented the dramatic clinical improvements observed in animal models by using systemically introduced xenogeneic hMSCs rather than allogeneic MSCs as a therapy in mouse models of multiple sclerosis and amyotrophic lateral sclerosis, inflammatory bowel disease, infarct, stroke, diabetes, and GVHD. Zhao et al., "Human mesenchymal stromal cells ameliorate the phenotype of SOD1-G93A ALS mice" *Cytotherapy* 9:414-426 (2007); Lee et al., "Multipotent stromal cells from human marrow home to and promote repair of pancreatic islets and renal glomeruli in diabetic NOD/scid mice" *Proc. Natl. Acad. Sci. USA* 103:17438-17443 (2006). A major advantage of demonstrating success using hMSCs in mouse models of human disease is that the possibility of gathering mechanistic data—beyond measuring biomarkers from readily obtainable body fluids or using noninvasive imaging technology may be realized, perhaps in the course of a clinical trial.

II. Alginate Microparticle Compound Delivery Platforms

In one embodiment, the present invention contemplates an alginate microparticle compound delivery system comprising at least one chemokine that is sustainably released at a desired site in a biomimetic fashion. Although it is not necessary to understand the mechanism of an invention it is believed that this sustained release profile creates a chemokine gradient that attracts cells (i.e., for example, multipotent stem cells) to a specific anatomical location.

Such system could be applied in all instances in which the presence of specific target cells could be desirable (i.e., for example, MSCs or an increased number of MSCs). For example, specific target cells are known to migrate to certain areas of the body as a reaction to physiological conditions including, but not limited to, reduction of local inflammation, promotion of tissue regeneration, repair of tissue damage, wound healing and/or promotion of local homeostasis. The system could be based on the rational design of polymer microparticles, such as PLGA microparticles, in which particle preparation parameters could be predictably tuned to modify the release profile, or on gel derived microparticles, such as hardened alginate microparticles, in which the gel density can be used to increase or decrease a compound release rate.

For example, the data presented herein shows that the chemokine PDGF has been encapsulated in microparticles of hardened alginate whose dimensions are in the micrometer scale. As the particles degrade, PDGF is released and progressively diffuses into the surrounding environment. It has also been demonstrated herein that PDGF release profiles may be changed as a result of microparticles containing different alginate concentrations. In general, it has been observed that higher alginate concentrations result in a slower release profile over time. Although it is not necessary to understand the mechanism of an invention, it is believed that these changes in release profile kinetics is a function of particle degradation. The data has also demonstrated that after release, the PDGF remains active and induces MSC migration towards the PDGF-releasing alginate microparticles.

Various PDGF release profiles were measured following incorporation of PDGF into microparticles having different concentrations of alginate. For example, when using 1% alginate microparticles there was an apparent trimodal release rate profile that showed an initial linear increase for approximately fifteen (15) days, followed by a two-and one half fold exponential increase in release rate on day fifteen that resulted an apparent termination in release a shown by a plateau in the measured released PDGF concentration (approximately 250 (pg/ml)/(mg of particle)) for the remainder of the test period (days 15-40). See, FIG. 1A.

Figure 1B:
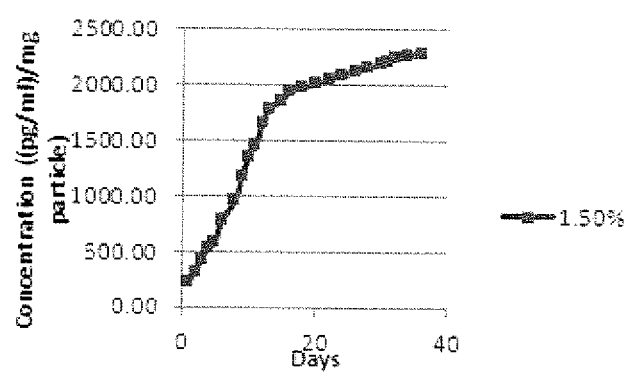

When using 1.5% alginate microparticles a bimodal release profile was observed. A first linear increase in release rate was observed during the first seventeen days followed by a second linear increase in release rate was observed between days seventeen-forty but at a substantially lower rate of increase. It should be noted that the released concentration of PDGF was ten-fold greater from the 1.5% alginate microparticles as opposed to the 1% alginate microparticles (approximately 2500 versus 250 (pg/ml)/(mg of particle) on day forty. See, FIG. 1B.

Figure 1C:
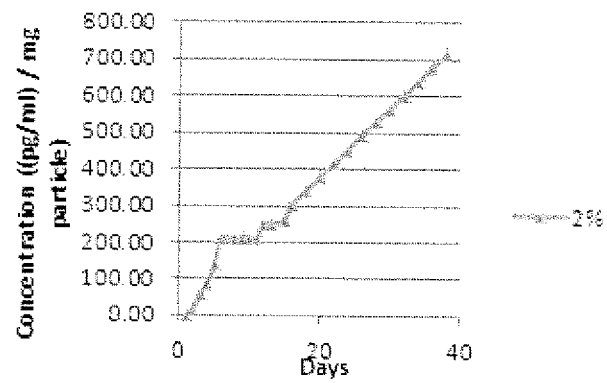

When using 2% alginate microparticles a near linear increase in release rate was observed during the entire forty day profile. However, there was a short plateau between approximately days ten-twenty where the release rate did not increase. When compared to the 1% and 1.5% alginate microparticles, these 2% alginate microparticles had a released concentration of PDGF of approximately 700 (pg/ml)/mg particle on day forty, thereby indicating that the overall release of PDGF was less than the 1.5% alginate particles but more than the 1% alginate particles. See, FIG. 1C.

Figure 1D:
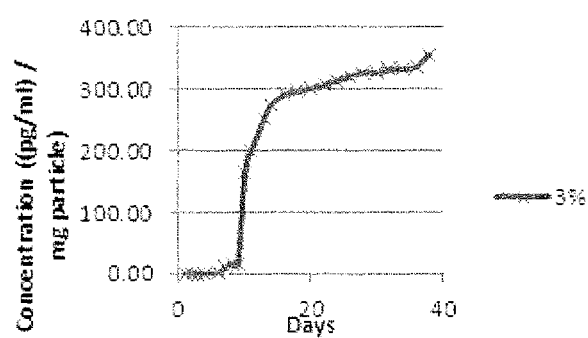

When using 3% alginate microparticles an exponential release function was observed, where the initial release rate is near zero for the first 5-7 days, followed by a near maximal release rate of PDGF between days 7-20. While the release profile during days 20-40 appears to be near zero, a slight release of residual PDGF was seen. Overall the 3% alginate microparticles show the lowest overall release as indicated by a measured concentration of released PDGF of approximately 300 (pg/ml)/(mg of particle) on day forty. See, FIG. 1D.

Figure 1E:
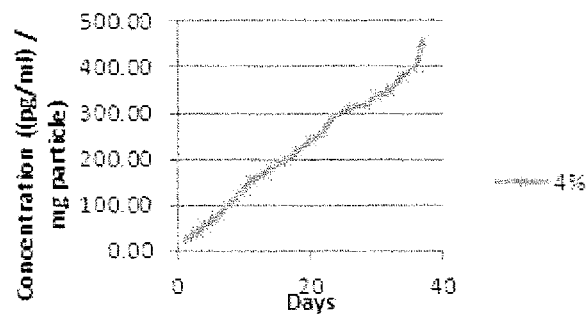

When using 4% alginate microparticles a unimodal release profile was observed during the entire forty day release period. Similar to the 3% alginate microparticles an low overall release was observed as indicated by a measured concentration of released PDGF of approximately 400 300 (pg/ml)/(mg of particle) on day forty. See, FIG. 1E.

Figure 2:
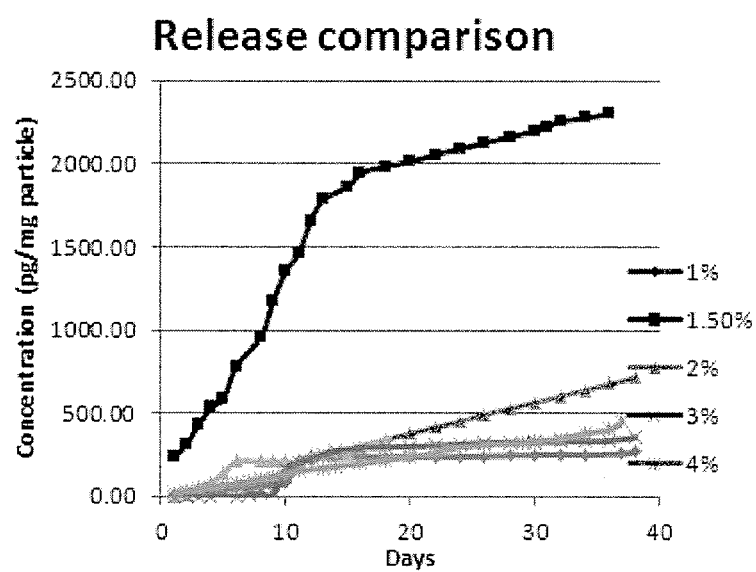
FIG. 2 illustrates a side-by-side comparison the data in FIGS. 1A-E demonstrating the effect of alginate concentration of the time course of a PDGF release profile.

With the exception of the 1.5% alginate microparticles, the general observation was that the total amount of released PDGF decreased in proportion to an increased amount of alginate in the microparticle. See, FIG. 2.

III. Applications of Alginate Microparticle Compound Delivery Systems

In some embodiments, the presently contemplated alginate microparticle compound delivery system for local recruitment of physiologically active cells (i.e., for example, MSCs) has numerous advantages. For instance, physiologically active cells are useful for medical conditions including, but not limited to, controlling, reducing or eliminating the inflammation and/or tissue damage caused by autoimmune diseases such as rheumatoid arthritis or psoriasis, or by inflammatory conditions such as inflammatory bowel disease or atherosclerosis. Furthermore, tissue injuries, from the smaller ones such as small burns or frostbites, to the more significant ones occurring in sports or motor vehicle accidents or during combat, all require tissue maintenance, remodeling, regeneration and the ability to control and enhance MSCs migration to the site of damage is crucial to favor wound healing and restoration of tissue structural integrity and functionality. In a tissue engineering perspective, the ability to recruit MSCs at the site of implant is crucial to ensure or enhance tissue regeneration, for instance to repair osteoarthritic cartilage, damaged bone, vascular tissue, respiratory or digestive ducts, or skin. Overall, the local recruitment of MSCs could promote homeostasis, stop disease/damage progression and favor tissue regeneration, either directly or by modulating the local environment and regulating nearby cell behavior.

A. Induced MSC Migration Model

Figure 3:
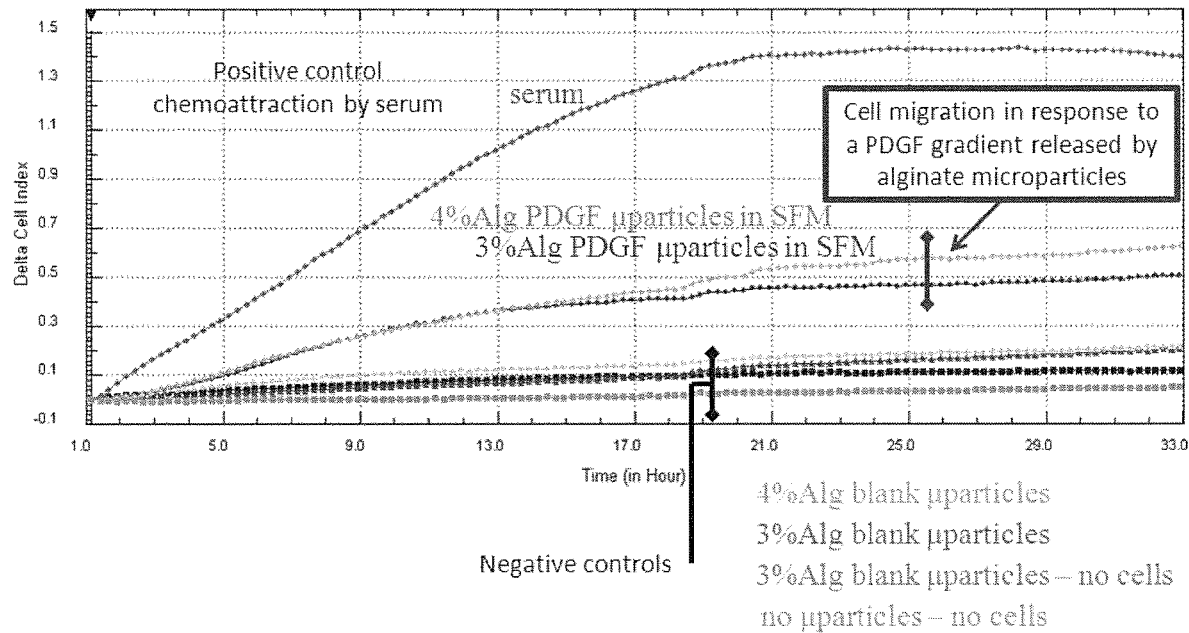
FIG. 3 presents exemplary data of MSC migration induced by PDGF release profiles from alginate microparticles as compared to normal serum and control alginate microparticles. Negative controls (Bottom four lines: top-to-bottom): 4% alginate blank microparticles with MSCs; 3% alginate blank microparticles with MSCs; 3% alginate blank microparticles without MSCs; no microparticles without MSCs. Positive control (Top line): Serum with MSCs. Experimental (Middle two lines): 4% alginate PDGF microparticle with MSCs; 3% alginate PDGF microparticle with MSCs. Cell migration was measured with an Xcelligence® transwell system (Roche) where the cells are counted as they migrate through a membrane moving from the cells-filled upper chamber to the microparticle-containing lower chamber of a transwell system.

Recruitment and migration of physiologically active cells to specific anatomical sites in the body is known to be mediated by gradients of specific compounds (i.e., for example, chemokines). The data presented herein uses the relationship between PDGF gradients and the recruitment and migration of MSCs to perform an in vitro migration study using an Xcelligence® transwell system (Roche). Cells are counted as they migrate through a membrane moving from the cells-filled upper chamber to the microparticle-containing lower chamber of a transwell system. Microparticles having alginate concentrations of 3% and 4% were either loaded with PDGF in accordance with Example VIII, or left empty to serve as a negative control. These migration experiments also utilized serum (known to contain PDGF) as a positive control. Both 3% and 4% alginate microparticles resulted in a linear increase in MSC migration over thirty-three day test period. While serum resulted in greater migration, the PDGF release from alginate microparticles resulted in a highly significant increase in migration as compared to random distribution as indicated by the blank microparticle data. See, FIG. 3.

B. Osteoarthritis Model

Osteoarthritis (OA) is a painful and disabling joint disease that affects millions of people worldwide, for which the ultimate treatment remains joint arthroplasty. Stopping or reversing tissue progressive damage and restoring tissue functionality would require the early identification of the disease and a targeted intervention. For these purposes, the identification of the specific processes involved in articular cartilage (AC) degeneration represents a crucial step. Since biochemical processes occur and pathological lesions start at the nanoscale, we adopted a nanotechnology approach.

In experiments designed to study the trafficking of hMSCs, mice were used that contained a single copy of a transgene (Tg) with an altered 3' regulatory region that causes chronic TNF-α overexpression, which leads to the development of severe erosive polyarthritis. Majumdar et al., "Characterization and functionality of cell surface molecules on human mesenchymal stem cells" *J. Biomed. Sci.* 10:228-241 (2003); and Rasmusson et al., "Mesenchymal stem cells inhibit the formation of cytotoxic T lymphocytes, but not activated cytotoxic T lymphocytes or natural killer cells" *Transplantation* 76:1208-1213 (2003). The TNF-Tg mice resemble RA patients in terms of their arthritis, and the arthritis phenotype is obviated by blocking with the anti-TNF-α monoclonal antibody infliximab.

Figure 4A:
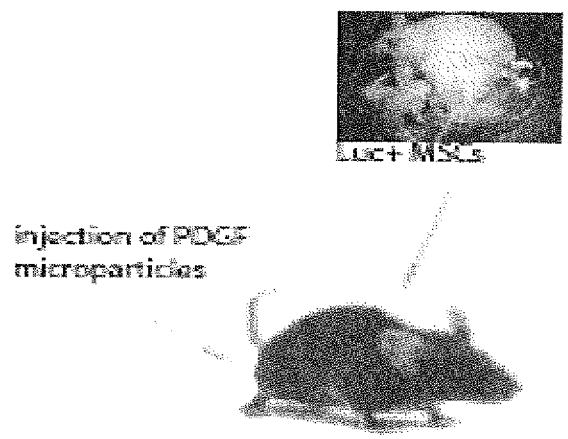
FIGS. 4A-4C present one possible experimental design to show joint homeostasis promotion that may follow from the migration of autologous MSCs using an injured articular joint mouse model.
Figure 4B:
Figure 4C:

Alginate microparticle release of PDGF would be expected to induce in vivo migration of MSCs. Mice may be given an intraarticular injection of mono-iodoacetate (MIA) in the left knee joint. MIA is a known compound to induce osteoarthritis. The mice are subsequently given an intraarticular injection of PDGF-loaded alginate microparticles in to the left knee joint coupled with a systemic injection of luciferin-labeled MSCs. Fluorescent imaging may demonstrate that the luciferin-labeled MSCs migrated to the left knee joint, documenting that the PDGF released from the alginate microparticles set up a biomimetic PDGF gradient such that the circulating MSCs were induced to migrate to the left knee joint. See, FIG. 4.

C. Osteochondral Plug Model

Osteochondral plug models provide a very good representation of an osteochondral unit present in human joint. For example, the model utilizes actual human tissues and the local defects that can be induced are a very close approximation of naturally occurring cartilage damage.

Figure 10:
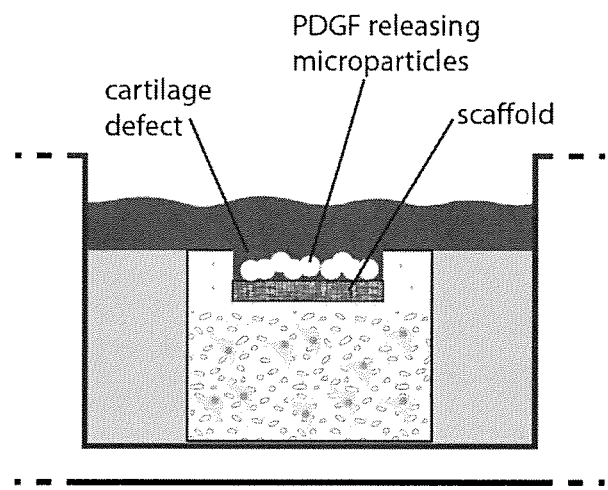
FIG. 10 presents one embodiment of an osteochondral plug model. Schematics of the osteochondral plug (bone in yellow and cartilage in white/light blue) are embedded in an agarose scaffold (pink). The defect in the cartilage contains a scaffold to which cells can attach and PDGF releasing microparticles.
Figure 11:
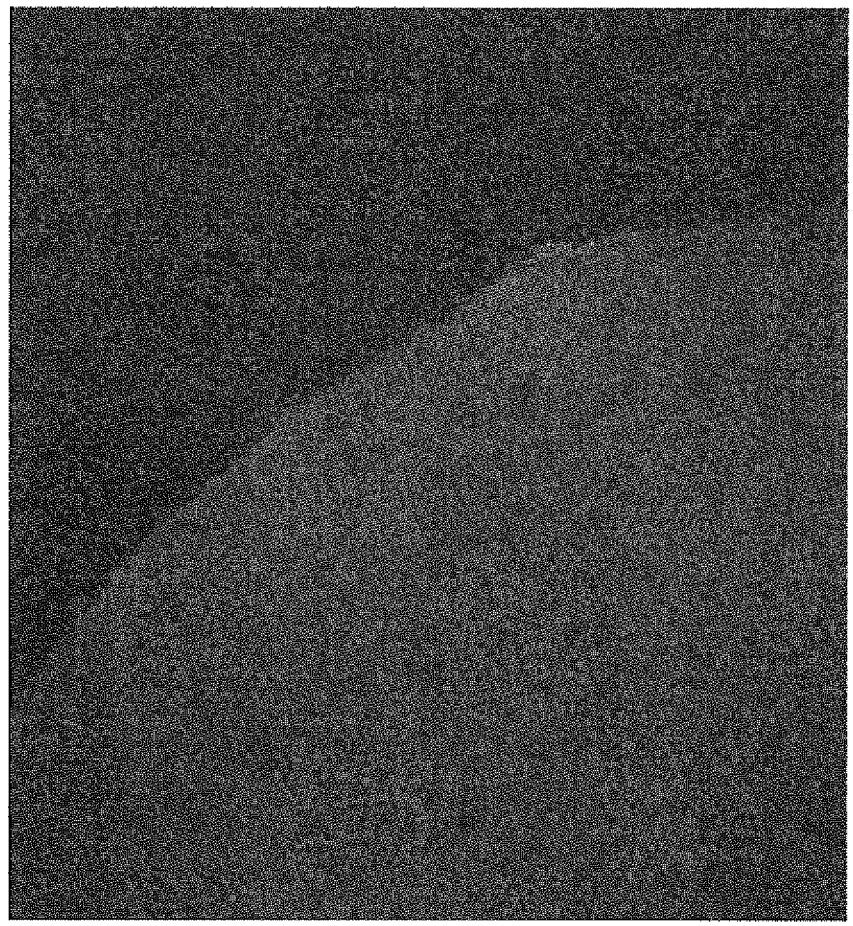
FIG. 11 presents exemplary data showing an osteochondral plug scaffold sheet with invading cells identified by the DAPI staining of their nuclei subsequent to the creation of a PDFG gradient.
Figure 12A:
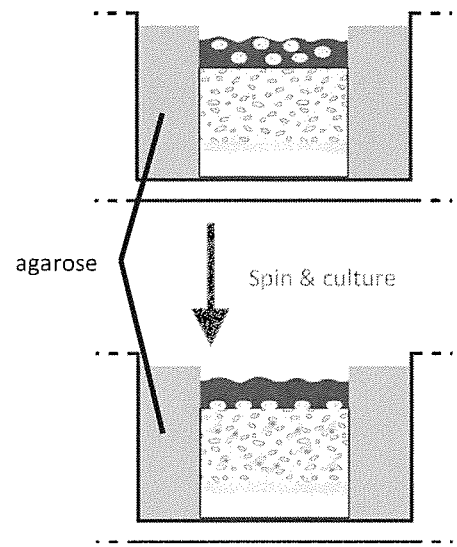
FIG. 12A illustrates the schematics of repopulation of decellularize osteochondral plugs.
Figure 12B:
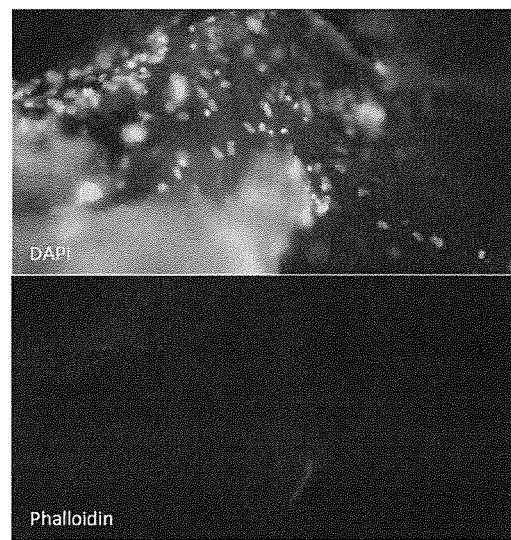
FIG. 12B presents exemplary data verifying the effectiveness of MSC repopulation by co-staining with Phalloidin TRITC and DAPI staining to show cytoskeletal and nuclear development.

In some embodiments, osteochondral plugs can be embedded in an agarose gel and cultured for several days. To reproduce osteoarthritis damage, a hole may be carved in the cartilage tissue, e.g., for example, at the center of the plug, to mimic a focal defect. Microparticles of the present invention can then be placed into the defect wherein a PDGF concentration gradient is created. See, FIG. 10. A thin Alvetex® scaffold may be placed within the defect to provide support for the migrating cells and a PDGF gradient has been created. In one embodiment, a PDGF gradient similar to what would be released by PDGF-loaded alginate microparticles has been created by periodic addition of excess PDGF to the culture media. As the culture media is positioned above the osteochondral plug, this orientation causes a local gradient through the cartilage hole. Consequently, when the scaffold support is extracted and examined, cells are observed to have invaded the scaffold in response to the PDGF gradient. See, FIG. 11. Although it is not necessary to understand the mechanism of an invention it is believed that cell migration seems to occur from the cartilage tissue direction rather than from the subchondral bone direction. Recently, migrating cells have been identified in cartilage that can differentiate into bone, cartilage, or adipose tissue, and they have been defined as cartilage mesenchymal stem cells. To verify the origin of the invading stem cells, osteochondral plugs have been decellularized, and only the bone part of the plug has been repopulated with hMSCs. See, FIG. 12.

Figure 13:
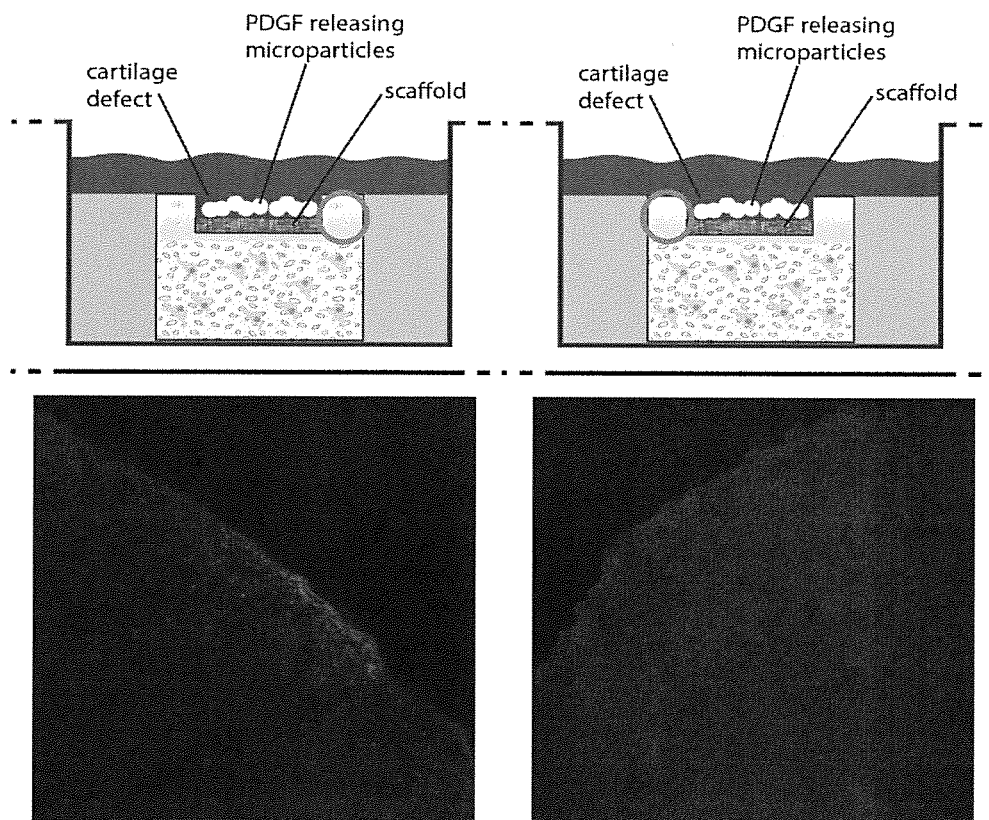
FIG. 13 illustrates schematics of a comparison of cell migration within the scaffold from native (upper left) and decellularized/repopulated (bone only) osteochondral plugs (upper right). Scaffolds implanted in native osteochondral plugs (lower left) present cell invasion (DAPI staining of cell nuclei), whereas scaffold in decellularized/repopulated osteochondral plugs (lower right) do not present cell invasion.

Osteochondral plugs may also be utilized to study cell migration within a cartilage defect by comparing native vs. decellularized/repopulated constructs. Over 10 days, only scaffolds in the native osteochondral plug show cell invasion, suggesting that, at least initially, stem cells can migrate to fill cartilage defects from the nearby cartilage rather than from the subchondral bone. See, FIG. 13.

At the completion of each model run, the invading cells may be characterized to confirm their sternness. Full osteochondral defects, damaging both cartilage and bone as may happen during joint damage, may also be studies in the osteochondral plug model to assess if a PDGF gradient increases MSCs migration from both bone and cartilage. After migration of MSCs is verified in all conditions, microparticles releasing a PDGF gradient rather than equivalent local administration of PDGF can also be tested in the osteochondral plug model.

D. Alginate Microparticle Validation Studies

Figure 5A:
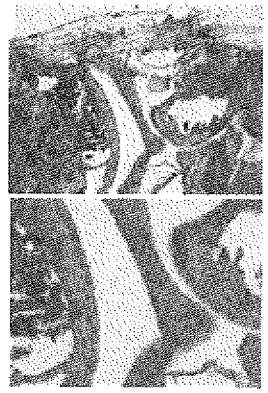
FIGS. 5A-5C present exemplary control data showing that blank microparticle administration does not result in articular cartilage damage.
Figure 5B:
Figure 5C:
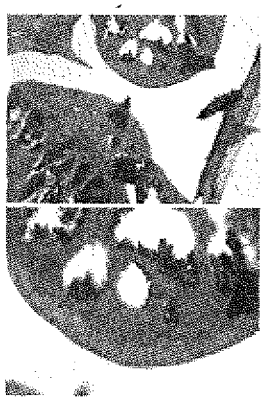

The reliability of the MIA mouse sports injury model was validated by intraarticular injection of blank alginate microparticles, where the appearance of the marine knee joint was unchanged after 3 days and 21 days after injection as compared to an intraarticular injection of physiologically buffered saline (PBS). See, FIG. 5.

Figure 6A:
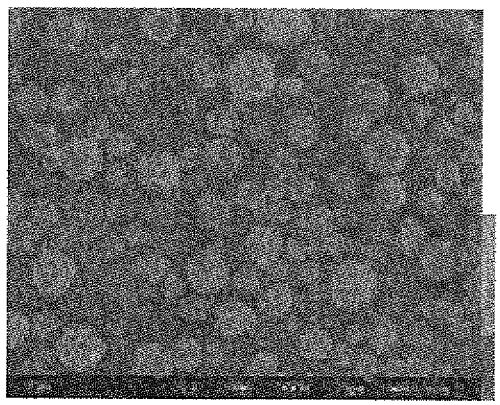
FIGS. 6A-6D present exemplary data demonstrating the correlation of microparticle erosion with PDGF release in vitro.
Figure 6B:
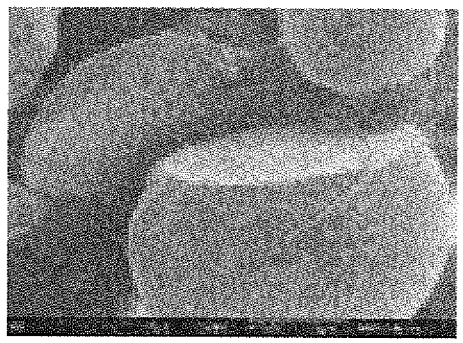
Figure 6C:
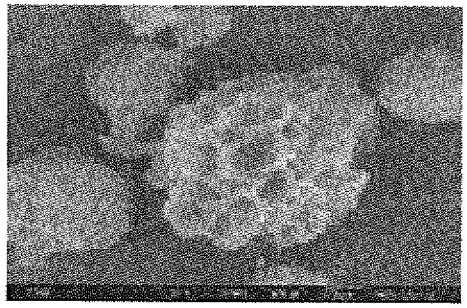
Figure 6D:

The reliability of alginate microparticle degradation, that is correlated with PDGF release, was validated using scanning electron microscopy of in vitro samples taken either on the first day or thirty days after in vitro microparticle incubation. Microparticles sampled on the first day of incubation are well rounded and have smooth surfaces. See, FIGS. 6A and 6B. On the other hand, microparticles sampled after thirty days of incubation are irregular in shape and have rough surfaces, consistent with a PDGF release mechanism that is dependent upon biodegradation. See, FIGS. 6C and 6D.

Figure 7A:
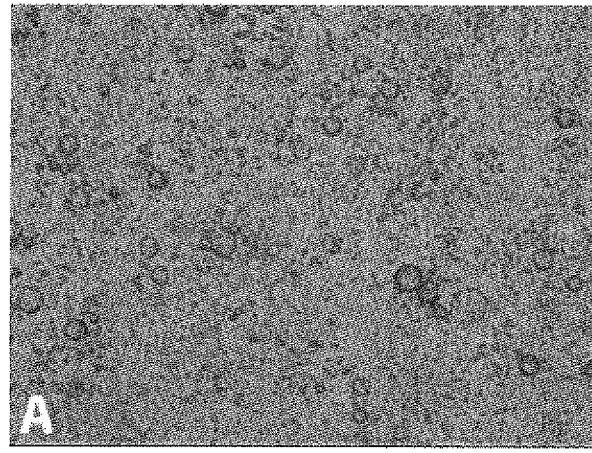
FIGS. 7A-7D present exemplary photomicrograph data of human MSCs/alginate microparticles in vitro mixtures that demonstrate non-cytotoxicity of the microparticles. The same image is shown under four different conditions.
Figure 7B:
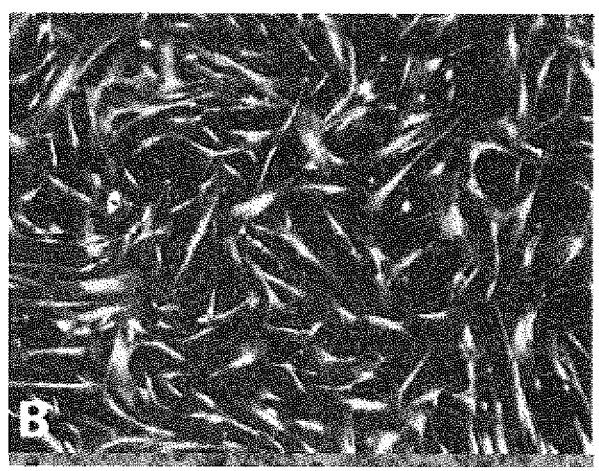
Figure 7C:
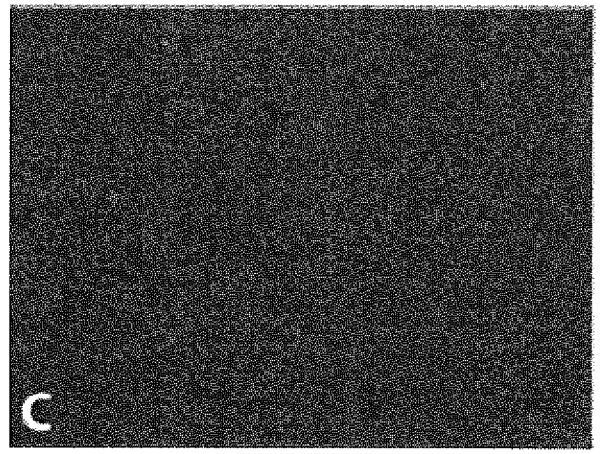
Figure 7D:
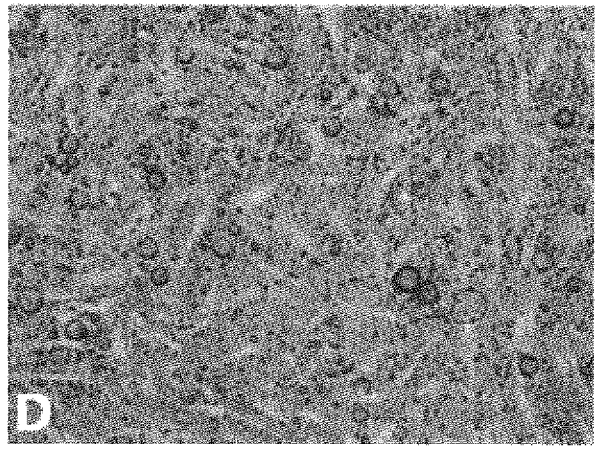

The lack of cytotoxicity of alginate microparticles on MSCs was determined by overlaying photomicrographs of the same image of a microparticle/human MSCs mixture under several conditions: i) a bright field image (See, FIG. 7A); ii) calcein staining (green) (See, FIG. 7B); and iii) ethidium heterodimer-1 staining (red) (See, FIG. 7C). When the photomicrographs of these three conditions were overlaid, there was clear co-localization of the green calcein staining with the locations of the MSCs in the bright field image. See, FIG. 7D. The lack of red staining after treatment with ethidium heterodimer-1 clearly demonstrates that no dead cells were detectable when the alginate microparticles were in contact with the human MSCs.

E. Tissue Regeneration

In one embodiment, the present invention contemplates a method for tissue regeneration comprising administering a chemokine-loaded microparticle to a patient having tissue damage. In one embodiment, tissue regeneration comprises wound healing. In one embodiment, tissue regeneration comprises tissue repair. In one embodiment the tissue regeneration comprises cartilage tissue regeneration. In one embodiment, the tissue regeneration comprises muscle tissue regeneration. Although it is not necessary to understand the mechanism of an invention it is believed that chemokine-loaded microparticle tissue regeneration is stem cell mediated.

hMSCs may be pericytes and, thus, would be present in all vascularized tissues. The presence of activated hMSCs at sites of inflammation or injury is understood, given that pericytes would be released from their endothelial interactions in such vascularized locations, although the relative number and source of hMSCs that are mobilized from remote sites, versus those that are derived from proximate vascularized sites, are topics of ongoing investigation. Singer et al., "Mesenchymal Stem Cells: Mechanisms of Inflammation" *Annu. Rev. Pathol. Mech. Dis.* 6:457-478 (2011).

Another characteristic of hMSCs is their ability to quell inflammation resulting from injury, allogeneic solid organ transplants, and autoimmune disease. hMSCs can effectively suppress the normal growth and expansion of stimulated T cells. Di Nicola et al., "Human bone marrow stromal cells suppress T-lymphocyte proliferation induced by cellular or nonspecific mitogenic stimuli" *Blood* 99:3838-3843 (2002). Consistent with in vitro studies, murine allogeneic MSCs are effective cellular therapies in the treatment of murine models of human disease. Several studies have documented the dramatic clinical improvements observed in animal models using systemically introduced hMSCs as a therapy in mouse models of multiple sclerosis, inflammatory bowel disease, infarct, stroke, and other devastating neurologic diseases, as well as diabetes. Lanz et al., "Mouse mesenchymal stem cells suppress antigen specific Th-cell immunity independent of indoleamine 2,3-dioxygenase 1 (IDO1)" *Stem Cells Dev.* 19: 657668 (2010); Constantin et al., "Adipose-derived mesenchymal stem cells ameliorate chronic experimental autoimmune encephalomyelitis" *Stein Cells* 27:2624-2635 (2009); Rafei et al., "Allogeneic mesenchymal stem cells for treatment of experimental autoimmune encephalomyelitis" *Mol. Ther.* 17:1799-1803 (2009); Zappia et al., "Mesenchymal stem cells ameliorate experimental autoimmune encephalomyelitis inducing T-cell anergy" *Blood* 106:1755-1761 (2005); Bai et al., "Human bonemarrow-derived mesenchymal stem cells induce Th2-polarized immune response and promote endogenous repair in animal models of multiple sclerosis" *Glia* 57:1192-1203 (2009); Ding et al., "Mesenchymal stem cells prevent the rejection of fully allogenic islet grafts by the immunosuppressive activity of matrix metalloproteinase-2 and -9" *Diabetes* 58:1797-1806 (2009); Gonzalez-Rey et al., "Human adult stem cells derived from adipose tissue protect against experimental colitis and sepsis" *Gut* 58:929-939 (2009); Gonzalez et al., "Adipose-derived mesenchymal stem cells alleviate experimental colitis by inhibiting inflammatory and autoimmune responses" *Gastroenterology* 136:978-989 (2009); Tanaka et al., "Exogenous administration of mesenchymal stem cells ameliorates dextran sulfate sodium—induced colitis via anti-inflammatory action in damaged tissue in rats" *Life Sci.* 83:771-79 (2008); Kang et al., "Interactions between human adipose stromal cells and mouse neural stem cells in vitro" *Brain Res. Dev. Brain Res.* 145:141-149 (2003); Zhao et al., "Human mesenchymal stromal cells ameliorate the phenotype of SOD1-G93A ALS mice" *Cytotherapy* 9:414-426 (2007); and Lee et al., "Multipotent stromal cells from human marrow home to and promote repair of pancreatic islets and renal glomeruli in diabetic NOD/scid mice" *Proc. Natl. Acad. Sci. USA* 103:17438-17443 (2006). These findings support the concept that hMSCs may be able to home to sites of inflammation, where dampening of inflammation can begin and regeneration of injured tissues leading to normal, scarless healing can proceed. In vivo, the current paradigm is that injury, inflammation, and/or foreign cells can lead to T cell activation, and those T cells produce proinflammatory cytokines including, but not limited to, TNF-$\alpha$, IFN-$\gamma$, IL-1$\alpha$, and IL-1$\beta$. Combinations of cytokines may also induce cell production of chemokines, some of which bind to CXCR3R expressing cells (including T cells) that colocalize with MSCs.

MSCs were originally evaluated for their capacity to repair skeletal defects first in experimental animal models and subsequently in human patients afflicted with osteogenesis imperfecta (OI), a genetic defect in bone and other tissues caused by mutations in the genes for type 1 collagen. Horwitz et al., "Isolated allogeneic bone marrow-derived mesenchymal cells engraft and stimulate growth in children with osteogenesis imperfecta: Implications for cell therapy of bone" *Proc Natl Acad Sci USA* 99:8932-8937 (2002). Subsequently, MSCs have demonstrated efficacy as therapeutic vectors in animal models of lung injury, kidney disease, diabetes, graft versus host disease, myocardial infarction, and various neurological disorders. Ortiz et al., "Mesenchymal stem cell engraftment in lung is enhanced in response to bleomycin exposure and ameliorates its fibrotic effects" *Proc Natl Acad Sci USA* 100:8407-8411 (2003). However, in a number of such reports, MSCs have affected tissue repair despite exhibiting low and/or transient levels of engraftment in vivo. For example, in the OI trials, children who received therapy showed measurable improvements in growth velocity, bone mineral density, and ambulation despite the fact that the levels of engrafted donor MSCs in bone, skin, and other tissues were less than 1%. Additionally, improvement in cardiac function was observed after infusion of human MSCs into immunodeficient mice with acute myocardial infarction despite the fact that no engrafted donor cells could be detected after 3 weeks postinjection Iso et al., "Multipotent human stromal cells improve cardiac function after myocardial infarction in mice without long-term engraftment" *Biochem Biophys Res Colman* 354:700-706 (2007). These and other studies suggest that capacity of MSCs to secrete soluble factors that alter the tissue microenvironment may play a more prominent role than their transdifferentiation in effecting tissue repair. Phinney et al., "Concise Review: Mesenchymal Stem/Multipotent Stromal Cells: The State of Transdifferentiation and Modes of Tissue Repair—Current Views" *Stem Cells* 25:2896-2902 (2007); and Prockop D J.," "Sternness" does not explain the repair of many tissues by mesenchymal stem/multipotent stromal cells (MSCs)" *Clin Pharmacol Ther* 82:241-243 (2007).

It is well established that MSCs produce a variety of cytokines and adhesion molecules that regulate aspects of hematopoiesis. Additionally, a recent analysis of the human and murine MSC transcriptome further revealed that the cells express transcripts encoding proteins that regulate a broad range of biological activities including angiogenesis, wound repair, immunity, and defense, as well as neural activities. Tremain et al., "MicroSAGE analysis of 2353 expressed genes in a single cell-derived colony of undifferentiated human mesenchymal stem cells reveals mRNAs of multiple cell lineages" *Stem Cells* 19:408-418 (2001); and Phinney et al., "Biological activities encoded by the murine mesenchymal stem cell transcriptome provide a basis for their developmental plasticity and broad clinical efficacy" *Stem Cells* 24:186-198 (2006). These studies revealed that MSCs express a number of proangiogenic factors as well as proteins that modulate endothelial cell migration. Cooperatively, these factors induce capillary proliferation and expansion of the sinusoidal space as well as vessel remodeling, a process involved in bone growth.

IV. Autoimmune Diseases

Autoimmune diseases arise from an inappropriate immune response of the body against substances and tissues normally present in the body (e.g., autoimmunity). This may be restricted to certain organs (e.g. in autoimmune thyroiditis) or involve a particular tissue in different places. The treatment of autoimmune diseases is typically with immunosuppression—medication that decreases the immune response. A large number of autoimmune diseases are recognized of which a representative number are discussed in detail below.

MSCs, otherwise known as multipotent mesenchymal stromal cells, are being examined for the treatment of autoimmune disease (AD) on the basis of their in vitro antiproliferative properties, immunoregulatory properties, efficacy in animal models, apparent low acute toxicity and the early positive anecdotal outcomes in human acute GVHD. Phase I/II clinical trials are underway in Crohn's disease and multiple sclerosis (MS) and are being planned for systemic lupus erythematosus (SLE), systemic sclerosis (SSc), systemic vasculitis and other AD. Open issues include patient selection, disease stage and activity, MSC source and expansion and long-term safety. Multidisciplinary groups are collaborating to ensure maximal use of available resources to establish the place, if any, of MSC in the treatment of AD. Tyndall et al., "Multipotent mesenchymal stromal cells for autoimmune diseases: teaching new dogs old tricks" *Bone Marrow Transplant.* 43(11):821-828 (2009).

A. Type 1 Diabetes

Type 1 diabetes is a prototypic, organ-specific autoimmune disease. Diverse antigen-specific immunotherapy using insulin or glutamic acid decarboxylase peptides and other immunotherapies, such as antibodies, fusion proteins, cytokines, regulatory T cells, small-molecule inhibitors, nonspecific immune modulators, or dietary modifications, have been attempted in human type 1 diabetes. Some of these immunotherapies delay the onset of diabetes or reduce insulin requirements or blood glucose level in patients with established type 1 diabetes. However, most of these immunotherapies failed to induce complete remission of established type 1 diabetes, which could be due to: 1) technical difficulties in the achievement of immune tolerance to diabetic autoantigens or in the inhibition of autoimmune responses to those antigens that can be applied to human patients without significant adverse effects; and 2) markedly reduced f3-cell mass at the time of disease onset that should be replenished. Kim et al., "Immunotherapeutic treatment of autoimmune diabetes" *Crit Rev Immunol.* 2013; 33(3):245-81.

Pancreas homeostasis is based on replication of differentiated cells in order to maintain proper organ size and function under changing physiological demand. Recent studies suggest that acinar cells, the most abundant cell type in the pancreas, are facultative progenitors capable of reverting to embryonic-like multipotent progenitor cells under injury conditions associated with inflammation. In parallel, it is becoming apparent that within the endocrine pancreas, hormone-producing cells can lose or switch their identity under metabolic stress or in response to single gene mutations. This new view of pancreas dynamics suggests interesting links between pancreas regeneration and pathologies including diabetes and pancreatic cancer. Ziv et al., "The plastic pancreas" *Dev Cell.* 26(1):3-7 (2013).

Vascular calcification is a regulated process that involves osteoprogenitor cells and frequently complicates common vascular disease such as atherosclerosis and diabetic vasculopathy. However, it is not clear if the vascular endothelium has a role in contributing osteoprogenitor cells to the calcific lesions. Two mouse models of vascular calcification, mice with gene deletion of matrix Gla protein (MGP), a BMP-inhibitor, and Ins2Akita/+ mice, a diabetes model showed that enhanced bone morphogenetic protein (BMP) signaling in both types of mice stimulates the vascular endothelium to contribute osteoprogenitor cells to the vascular calcification.

The enhanced BMP signaling results in endothelial-mesenchymal transitions and the emergence of multipotent cells, followed by osteoinduction. Endothelial markers co-localize with multipotent and osteogenic markers in calcified arteries by immunostaining and fluorescence-activated cell sorting. Lineage tracing using Tie2-Gfp transgenic mice supports an endothelial origin of the osteogenic cells. Enhancement of MGP expression in Ins2Akita/+ mice, as mediated by an Mgp transgene limits the generation of multipotent cells. Moreover, MGP-depleted human aortic endothelial cells in vitro acquire multipotency rendering the cells susceptible to osteoinduction by BMP and high glucose. These data suggest that the endothelium is a source of osteoprogenitor cells in vascular calcification that occurs in disorders with high BMP activation such as deficiency of BMP inhibitors and diabetes. Yao et al., "A Role for the Endothelium in Vascular Calcification" Circ. Res. (Jul. 12, 2013) [Epub ahead of print]

Type 1 diabetes can occur at any age. However, it is most often diagnosed in children, adolescents, or young adults. Insulin is a hormone produced by special cells, called beta cells, in the pancreas. The pancreas is found behind your stomach. Insulin is needed to move blood sugar (glucose) into cells, where it is stored and later used for energy. In type 1 diabetes, beta cells produce little or no insulin. Without enough insulin, glucose builds up in the bloodstream instead of going into the cells. The body is unable to use this glucose for energy. This leads to the symptoms of type 1 diabetes that include but are not limited to, thirst, hunger, fatigue, blurred eyesight, loss of feeling or tingling in the feet, unexplained weight loss and/or frequent urination.

B. Alopecia Areata

Alopecia areata (AA) is an autoimmune disease resulting in the premature arrest of the follicular growth cycle clinically resulting in patchy, non-scarring hair loss. The presence of a dense follicular T cell infiltrate and variations in cytokines have led to the hypothesis that T cell activation and alterations in inflammatory mediators participate in the etiopathogenesis of the disease. AA pathogenesis is believed to have a dominant TH1-mediated component, with potential involvement of the TH17 pathway. However, a fully integrated view of intersecting cytokine networks that support the autoimmune response in AA is lacking. A more precise understanding of cytokine pathways in disease is required to rationally explore cytokine targeted treatment strategies. Giordano et al., "Cytokine pathways and interactions in alopecia areata" Eur J Dermatol. Jun. 24, 2013. [Epub ahead of print].

Recent work has focused on the hair follicle as the main source of multipotent stem cells in the skin. The hair follicle bulge contains multipotent stem cells that can form the epidermis, hair follicles and sebaceous glands and help in repopulation of the epidermis after injury. The localization of these stem cells to the bulge area may explain why some types of inflammatory alopecia cause permanent loss of hair (cicatricial alopecia) (such as lichen planopilaris and discoid lupus erythematosus), while others (such as alopecia areata) are reversible (noncicatricial alopecia). The lack of distinctive bulge morphology in human hair follicles has hampered studies of bulge cells. To date, the best marker for bulge stem cells in human hair is cytokeratin (CK) 15; human bulge cells have been reported to express CK15 selectively throughout all stages of the hair cycle in different types of follicles. There is direct evidence in the mouse, and indirect evidence in the human, that compromising the integrity of the sebaceous gland and/or bulge is important in the development of alopecia. Several interesting studies have been done in the last few years to investigate the role of stem cells in alopecia, especially nonscarring types. The role of stem cells in the pathogenesis of alopecia (scarring and nonscarring) has recently been reviewed. Al-Refu K., "Stem cells and alopecia: a review of pathogenesis" Br J Dermatol. 167(3):479-484 (2012).

Clinical conditions causing hair loss, such as androgenetic alopecia, alopecia areata, and scarring alopecia, does not rest solely with its ability to produce hair. Hair follicles are self-renewing and contain reservoirs of multipotent stem cells that are capable of regenerating the epidermis and are thought to be utilized in wound healing. Millar S E, "Molecular mechanisms regulating hair follicle development" J Invest Dermatol. 118(2):216-225 (2002).

The cause of alopecia areata is unknown but can occur in men, women and children. About 1 in 5 people with this condition have a family history of alopecia. In a few people, hair loss may occur after a major life event such as an illness, pregnancy, or trauma. Forms of alopecia include, but are not limited to, alopecia areata—patches of hair loss; alopecia totalis—complete loss of scalp hair, and/or alopecia universalis—total loss of all body hair.

Hair loss is usually the only symptom of alopecia, but a burning sensation or itching may also be present Alopecia areata usually begins as one to two patches of hair loss. Hair loss, is most often seen on the scalp. It may also occur in the beard, eyebrows, and arms or legs in some people. Patches where hair has fallen out are smooth and round in shape. They may be peach-colored. Hairs that look like exclamation points are sometimes seen at the edges of a bald patch.

C. Systemic Lupus Erythematosus

Systemic lupus erythematosus (SLE) is a prototypic autoimmune disease, characterized by the production of autoantibodies against multiple organs. MicroRNAs (miRNAs) are non-coding, single-stranded small RNAs that post-transcriptionally regulate gene expression. Evidence is accumulating that miRNAs play a role in the pathogenesis of SLE. miRNAs may also play regulatory roles in the DNA methylation pathway, type I interferon pathway, estrogen and regulatory T-cells in the pathogenesis of SLE. Ma et al., "MicroRNAs in the pathogenesis of systemic lupus erythematosus" Int J Rheum Dis. 2013 16(2):115-121.

Bone marrow-derived mesenchymal stem cells (BM-MSCs) are multipotent stem cells characterized by immunomodulatory properties and therefore may be useful in the treatment of immune-mediated diseases. One study was undertaken to assess the influence of murine BM-MSCs on the activation of B cells in (NZB×NZW)F(1) mice as an animal model of systemic lupus erythematosus (SLE). The in vitro effects of BM-MSCs was evaluated on the proliferation and differentiation to plasma cells of splenic mature B cell subsets, namely follicular and marginal zone B cells isolated from (NZB×NZW)F(1) mice. Lupus mice were also treated with BM-MSCs, and serum autoantibodies, proteinuria, histologic changes in the kidney, and survival rates were monitored. BM-MSCs inhibited antigen-dependent proliferation and differentiation to plasma cells of follicular and marginal zone B cells in vitro. This inhibitory effect was dependent on interferon-γ (IFNγ) and was mediated by cell-to-cell contact, involving the programmed death 1 (PD-1)/PD ligand pathway. In vivo treatment with BM-MSCs did not affect the levels of anti-double-stranded DNA antibodies or proteinuria. However, a reduction in glomerular immune complex deposition, lymphocytic infiltration, and glomerular proliferation was observed. These findings indicate that BM-MSCs affect B cell receptor-dependent activation of both follicular and marginal zone B cells from lupus mice.

This inhibitory effect is IFNγ-dependent and cell contact-dependent. MSCs in vivo do not affect the production of autoantibodies, the level of proteinuria, or the mortality rates. Nonetheless, the observed improvement in histologic findings in the kidney supports the potential role of MSCs in the prevention of glomerular damage. Schena et al., "Interferon-γ-dependent inhibition of B cell activation by bone marrow-derived mesenchymal stem cells in a murine model of systemic lupus erythematosus" *Arthritis Rheum.* 62(9): 2776-2786 (2010).

Hematologic abnormalities in patients with systemic lupus erythematosus (SLE) were studied before treatment, using an in vitro bone marrow progenitor cell assay. In 10 patients with SLE, there was a decrease in the number of multipotent hemopoietic colonies. Multipotent colony formation was suppressed by the addition of T cells from the patients with SLE. The culture supernatant of phytohemagglutinin stimulated SLE leukocytes had diminished activity to support the multipotent colony formation. These results suggest that the hematologic abnormalities in SLE occur at the multipotent stem cell level. The T cell mediated suppression of hemopoietic progenitor cells and the diminished activity of humoral factors released from SLE leukocytes may play some role in the pathogenesis of hematologic abnormalities in SLE. Otsuka et al., "Multipotent hemopoietic progenitor cells in patients with systemic lupus erythematosus" *J Rheumatol.* 15(7):1085-1090 (1988).

SLE is a long-term autoimmune disorder that may affect the skin, joints, kidneys, brain, and other organs. SLE is much more common in women than men. It may occur at any age, but appears most often in people between the ages of 10 and 50. African Americans and Asians are affected more often than people from other races.

Symptoms vary from person to person, and may come and go. Almost everyone with SLE has joint pain and swelling. Some develop arthritis. Frequently affected joints are the fingers, hands, wrists, and knees. Common SLE symptoms include, but are not limited to, chest pain when taking a deep breath, fatigue, unexplained fever, general discomfort, uneasiness, malaise, hair loss, mouth sores, sunlight sensitivity, skin rash (e.g., a "butterfly" rash over the cheeks and bridge of the nose), or swollen lymph nodes.

D. Sjogren's Syndrome

Sjogren syndrome is an autoimmune disorder in which the glands that produce tears and saliva are destroyed, causing dry mouth and dry eyes. However, the condition may affect many different parts of the body, including the kidneys and lungs.

One study suggested that bone marrow mesenchymal stem cells in SS-like NOD/Ltj mice and human patients were defective in immunoregulatory functions. Treatment with mesenchymal stem cells (MSCs) suppressed autoimmunity and restored salivary gland secretory function in both mouse models and SS patients. MSC treatment directed T cells toward Treg and Th2, while suppressing Th17 and Tfh responses, and alleviated disease symptoms. Infused MSCs migrated toward the inflammatory regions in a stromal cell-derived factor-1-dependent manner, as neutralization of stromal cell-derived factor-1 ligand CXCR4 abolished the effectiveness of bone marrow mesenchymal stem cell treatment. Collectively, this study suggests that immunologic regulatory functions of MSCs play a role in SS pathogenesis, and allogeneic MSC treatment may provide an effective, and safe therapy for patients with SS. Xu et al., "Allogeneic mesenchymal stem cell treatment alleviates experimental and clinical Sjogren syndrome" *Blood* 11; 120(15):3142-3151 (2012).

Symptoms may include, but are not limited to, dryness of the mouth and eyes, itching eyes, feeling that something is in the eye, difficulty swallowing or eating, loss of sense of taste, difficulty speaking, thick or stringy saliva, mouth sores or pain, hoarseness, fatigue, fever, Color change of hands or feet, joint pain or joint swelling and/or swollen glands.

E. Rheumatoid Arthritis

Rheumatoid arthritis (RA) is a chronic, inflammatory, autoimmune disease with typical onset between the ages of 40 and 50 years, characterized by chronic inflammation in synovial joints. Effective treatment for RA is lacking because the clear etiology and pathogenesis of RA have not been fully elucidated. Cytokine-mediated immunity has been found to play an important role in the pathogenesis of various autoimmune diseases such as RA. Recently, IL-32 is identified with high expression in RA patients and mice models of experimental inflammatory arthritis. IL-32 is recognized to play a crucial role in RA with pro-inflammatory effects. Furthermore, interventions for blocking IL-32 in RA seem possible and applicable. Therefore, targeting IL-32 may give therapeutic potential. Xu et al., "IL-32 with potential insights into rheumatoid arthritis" *Clin Immunol.* 2013 147(2):89-94.

Increasing levels of physical activity (PA) have been shown to decrease inflammation, reduce pain, increase functional ability and improve self-esteem in people with RA. Health behavior change (HBC) interventions have recently shown promise in facilitating the promotion of PA within a range of long-term conditions. There is currently no evidence synthesis relating to HBC interventions to increase PA in the RA population. Cramp et al., "Health Behaviour Change Interventions for the Promotion of Physical Activity in Rheumatoid Arthritis: A Systematic Review" *Musculoskeletal Care* May 7, 2013 [Epub ahead of print].

Multipotent mesenchymal stromal cells (MSCs) have raised interest mainly because of cartilage/bone differentiation potential which is now partly eclipsed by their capacity to counteract inflammation and suppress host immune responses as well as to prevent fibrosis. MSCs have been identified within joint tissues including synovium, cartilage, subchondral bone, periosteum or adipose tissue. They are characterized by their phenotype and their ability to differentiate into three lineages, chondrocytes, osteoblasts and adipocytes. MSCs have also paracrine effects through the secretion of a number of cytokines and growth factors. This may explain the trophic effects that may be of therapeutic value for rheumatic diseases including OA and RA. On the other hand, MSCs have been associated with tumour growth. MSCs migrate to the tumour stroma, express chemokines involved in the attraction of carcinoma cells in metastasis. Indeed, the aim of this review is not only to focus on new potential therapeutic applications in osteo-articular diseases, but also to assess the potential risk of MSC-based cell therapy. Bouffi et al., "Multipotent mesenchymal stromal cells and rheumatoid arthritis: risk or benefit?" *Rhetumatology (Oxford)* 48(10):1185-1189 (2009).

MSCs demonstrate immunosuppressive functionality by suppressing T- and B-cell responses following activation by cytokines such as IL-6 and IL-1α. They also can be induced to exert pro-inflammatory effects in the presence of acute inflammatory environment due to the actions of TNF-α and 11-N-γ. In inflammatory joint diseases such as rheumatoid arthritis, MSCs in bone marrow migrate to joints by a TNF-α-dependent mechanism and may be in part responsible for the disease process. MSCs have also been demonstrated in increased numbers in periarticular tissues in osteoarthritis, which may reflect an attempt at joint regeneration. MacFarlane et al., "Anti-inflammatory role and immunomodulation of mesenchymal stem cells in systemic joint diseases: potential for treatment" *Expert Opin Ther Targets* 17(3):243-254 (2013).

RA usually affects joints on both sides of the body equally. Wrists, fingers, knees, feet, and ankles are the most commonly affected. The disease often begins slowly, usually with only minor joint pain, stiffness, and fatigue.

Joint symptoms of RA may include, but are not limited to, morning stiffness, which lasts more than 1 hour, unused joints feel warm, tender, and stiff, loss of joint range of motion, joint deformation, pleurisy, dry eyes and mouth, eye burning, itching, and discharge, skin nodules, numbness, tingling, or burning in the hands and feet, and/or sleep difficulties.

F. Antiphospholipid Antibody Syndrome

Antiphospholipid antibody syndrome (APS) is an autoimmune disease that leads to arterial and/or venous thrombosis, recurrent pregnancy loss and persistently positive aPLs. Antibodies against antigenic anionic phospholipid protein complexes are detected by their reactivity to the anionic phospholipids (or protein phospholipid complexes) in solid-phase immunoassays or by their property of inhibiting phospholipid-dependent coagulation reactions (the "lupus anticoagulant" effect).

Patients with clinical manifestations highly suggestive of APS but persistently negative conventional aPLs are classified as having seronegative APS. Ongoing research has revealed the existence of non-criteria antibodies proposed to be relevant to APS and that can be potentially included in the disease's classification criteria. Some antibodies of this heterogeneous aPL family may include, but are not limited to, antibodies to a zwitterionic phospholipid, namely phosphatidylethanolamine, phospholipid-binding plasma proteins, phospholipid-protein complexes and anionic phospholipids other than cardiolipin. Although these molecules can increase the diagnostic yield of APS, their clinical relevance is still debatable and needs to be confirmed by interlaboratory efforts toward standardizing diagnostic tools, in addition to experimental data and larger longitudinal studies. Nayfe et al., "Seronegative antiphospholipid syndrome" Rheumatology (Oxford). Mar. 15, 2013. [Epub ahead of print].

Systemic lupus erythematosus (SLE) is the most common disease associated with antiphospholipid syndrome (APS). We, therefore, evaluated 46 patients with refractory SLE treated by autologous hematopoietic stem cell transplantation (HSCT) for a history of APS prior to transplantation. The prevalence of SLE-related APS in our patient population was 61% (28 of 46 patients with refractory SLE). Nineteen of 28 patients with APS had lupus anticoagulant (LA) or high titers of anticardiolipin antibodies (ACLAs), either immunoglobulin (Ig)G or IgM, when evaluated at study entry. Six of 8 evaluable LA+ patients became and remained LA−; 5 of 7 initially ACLA IgG+ patients and 9 of 11 ACLA IgM+ patients demonstrated normalization of ACLA titers when followed after HSCT. Eighteen of 22 patients refractory to chronic anticoagulation discontinued anticoagulation therapy a median of 4 months after transplantation; 78% of them remained free of thrombotic events and in complete SLE remission for up to 78 months (median, 15 months) after HSCT. There was no treatment-related mortality. Autologous HSCT may be performed safely in patients with APS and appears to be effective therapy for eliminating ALPAs and preventing thrombotic complications in patients with SLE. Statkute et al., "Antiphospholipid syndrome in patients with systemic lupus erythematosus treated by autologous hematopoietic stem cell transplantation" *Blood* 106(8):2700-2709 (2005).

G. Multiple Sclerosis

Multiple sclerosis (MS) affects women more than men. The disorder is most commonly diagnosed between ages 20 and 40, but can be seen at any age. MS is caused by damage to the myelin sheath, the protective covering that surrounds nerve cells. When this nerve covering is damaged, nerve signals slow down or stop. The nerve damage is caused by inflammation. Inflammation occurs when the body's own immune cells attack the nervous system. This can occur along any area of the brain, optic nerve, and spinal cord.

Multiple sclerosis (MS) is assumed to be an autoimmune disease initiated by autoreactive T cells that recognize central nervous system antigens. Although adaptive immunity is clearly involved in MS pathogenesis, innate immunity increasingly appears to be implicated in the disease. Natural killer (NK) cells may be involved in immunoregulation in MS, leading to the question of whether a particular NK cell subtype will account for this effect. Changes of NK cell functionality in MS can be associated with MS activity, and depletion of NK cells exacerbated the course of disease in a murine model of MS, experimental autoimmune encephalomyelitis. A deficiency and transient "valleys" in NK cell killing activity in human MS, may coincide with symptomatic relapse. However, the molecular basis of the defect in killing activity has not been determined. For example, perforin is expressed in CD16(+) NK cells while there is an inverse relationship between myelin loaded phagocytes and the proportion of CD16(+) NK cells expressing perforin in the circulation. This inverse relationship is consistent with a role for NK cell killing activity in dampening autoimmunity. On the other hand, it has been broadly reported that first line MS therapies, such as interferon-beta, glatiramer acetate as well as escalation therapies such as fingolimod, daclizumab, or mitoxantrone seem to affect NK cell functionality and phenotype in vivo. Chanvillard et al., "The role of natural killer cells in multiple sclerosis and their therapeutic implications" *Front Immunol.* 2013; 4:63.

Systemic delivery of multipotent mesenchymal stem cells (MSC) may be of benefit in the treatment of neurological diseases, including multiple sclerosis (MS). Certainly, animal studies have demonstrated functional benefits following MSC transplantation, although the mechanisms by which MSCs migrate to lesions and stimulate repair remain unknown. Chemokines stimulate migration in other settings. In one study, a systematic exploration of the migratory and proliferative responses of human MSCs (hMSC) to chemokines expressed in MS lesions was reported. The data showed that chemokines trigger hMSC migration and that RANTES and IP-10 promote hMSC proliferation. Rice et al., "Adult human mesenchymal cells proliferate and migrate in response to chemokines expressed in demyelination" *Cell Adh Migr.* 4(2):235-240 (2010)

Adult subventricular zone (SVZ)-derived neural stem cells (NSCs) have therapeutic effects in experimental autoimmune encephalomyelitis, an animal model of multiple sclerosis. However, SVZ precursor cells as a source of NSCs are not readily accessible for clinical application. One study has demonstrated that NSCs derived from bone marrow (BM) cells exhibit comparable morphological properties as those derived from. SVZ cells and possess a similar ability to differentiate into neurons, astrocytes, and oligodendrocytes both in vitro and in vivo. Both types of NSCs suppressed chronic experimental autoimmune encephalomyelitis to a comparable extent on transplantation. Mechanisms underlying the therapeutic effects of NSCs include immunomodulation in the periphery and the central nervous system (CNS), neuron/oligodendrocyte repopulation by transplanted cells, and enhanced endogenous remyelination and axonal recovery. Furthermore, evidence for the transdifferentiation of transplanted BM-NSCs into neural cells in the CNS was provided, while no fusion of these cells with host neural cells was detected. Yang et al., "Evaluation of bone marrow- and brain-derived neural stem cells in therapy of central nervous system autoimmunity" *Am J Pathol.* 177(4):19892001 (2010).

Symptoms vary, because the location and severity of each attack can be different. Episodes can last for days, weeks, or months. These episodes alternate with periods of reduced or no symptoms (remissions). Fever, hot baths, sun exposure, and stress can trigger or worsen attacks. It is common for the disease to return (relapse). However, the disease may continue to get worse without periods of remission. Because nerves in any part of the brain or spinal cord may be damaged, patients with multiple sclerosis can have symptoms in many parts of the body. Symptoms of MS include, but are not limited to, loss of balance, muscle spasms, numbness or abnormal sensation in any area, problems moving arms or legs, problems walking, problems with coordination and making small movements, tremor in one or more arms or legs, weakness in one or more arms or legs, constipation, stool leakage, difficulty beginning to urinate, frequent need to urinate, strong urge to urinate, incontinence, double vision, eye discomfort, uncontrollable rapid eye movements, vision loss, facial pain, painful muscle spasms, tingling, crawling, or burning feeling in the arms and legs, decreased attention span, poor judgment, and memory loss, difficulty reasoning and solving problems, depression or feelings of sadness, dizziness and balance problems, hearing loss, slurred or difficult-to-understand speech, trouble chewing and swallowing and/or fatigue.

H. Crohn's Disease

Crohn's disease is a form of inflammatory bowel disease (IBD). It usually affects the intestines, but may occur anywhere from the mouth to the end of the rectum (anus). The exact cause of Crohn's disease is unknown but is believed to be an autoimmune disorder. People with Crohn's disease have ongoing (chronic) inflammation of the gastrointestinal tract (GI tract). Crohn's disease may involve the small intestine, the large intestine, the rectum, or the mouth. The inflammation causes the intestinal wall to become thick.

Crohn's disease is often considered an autoimmune condition, based on the observations of a histopathological inflammatory process in the absence of identifiable causal microorganism(s) and that immune-modulating therapeutics result in diminished host-directed inflammatory pathology. However, the evidence for a self-targeted immune response is unproven; thus, the instigating and perpetuating forces that drive this chronic inflammation remain unknown. In recent years, a convergence of findings from different fields of investigation has led to a new paradigm, where Crohn's disease appears to be the consequence of an intrinsic innate immune deficiency. While genomic/postgenomic studies and functional immunologic investigations offer a common perspective, critical details of the processes involved require further elaboration. Vinh et al., "Crohn's as an immune deficiency: from apparent paradox to evolving paradigm" Expert Rev Clin Immunol. 2013 9(1):17-30.

Crohn's disease is a complex disease in which genome, microbiome, and environment interact to produce the immunological background of the disease. Disease in childhood is more extensive and characterized by a rapid progression, leading to severe repercussions in the course of the disorder. Several genetic variations have been associated with an increased risk of developing the disease and most of these are also implicated in other autoimmune disorders. The gut has many tiers of defense against incursion by lumina' microbes, including the epithelial barrier and the innate and adaptive immune responses. Moreover, recent evidence shows that bacterial and viral infections, as well as inflammasome genes and genes involved in the autophagy process, are implicated in Crohn's disease pathogenesis. Marcuzzi et al., "Genetic and functional profiling of Crohn's disease: autophagy mechanism and susceptibility to infectious diseases" *Biomed Res Int.* 2013; 2013: 297501.

Although ongoing clinical trials utilize systemic administration of bone-marrow mesenchymal stromal cells (BM-MSCs) in Crohn's disease (CD), nothing is known about the presence and the function of mesenchymal stromal cells (MSCs) in the normal human bowel. MSCs are bone marrow (BM) multipotent cells supporting hematopoiesis with the potential to differentiate into multiple skeletal phenotypes. A recently identified new marker, CD146, allowing to prospectively isolate MSCs from BM, renders also possible their identification in different tissues. In order to elucidate the presence and functional role of MSCs in human bowel normal adult colon sections were analyzed and MSCs isolated. In colon sections, resident MSCs form a net enveloping crypts in lamina propria, coinciding with structural myofibroblasts or interstitial stromal cells. Nine sub-clonal CD146(+) MSC lines were derived and characterized from colon biopsies, in addition to MSC lines from five other human tissues. In spite of a phenotype qualitative identity between the BM- and C-MSC populations, they were discriminated and categorized. Similarities between C-MSC and BM-MSCs are represented by: Osteogenic differentiation, hematopoietic supporting activity, immune-modulation, and surface-antigen qualitative expression. The differences between these populations are: C-MSCs mean intensity expression is lower for CD13, CD29, and CD49c surface-antigens, proliferative rate faster, life-span shorter, chondrogenic differentiation rare, and adipogenic differentiation completely blocked. Briefly, BM-MSCs, deserve the rank of progenitors, whereas C-MSCs belong to the restricted precursor hierarchy. The presence and functional role of MSCs in human colon provide a rationale for BM-MSC replacement therapy in CD, where resident bowel MSCs might be exhausted or diverted from their physiological functions. Signore et al., "Identity and ranking of colonic mesenchymal stromal cells" *J Cell Physiol.* 227(9):3291-3300 (2012).

Because of the capacity of mesenchymal stromal cells (MSC) to modulate the immune response and promote tissue repair, these cells may be useful in the treatment of Crohn's disease (CD). One study performed an in vitro characterization of MSCs from active CD patients where Bone marrow MSCs were expanded ex vivo and investigated for clonogenic efficiency, proliferative capacity, morphology, immunophenotype, differentiation potential, genetic stability and ability to suppress in vitro proliferation of both autologous and allogeneic lymphocytes to polyclonal mitogens. Results were compared with those of BM MSC of four healthy donors (HD). Colony-forming unit-fibroblast (CFU-F) frequency and proliferative capacity were comparable in CD and HD MSC. CD MSC showed typical spindle-shaped morphology and differentiated into osteoblasts, adipocytes and chondrocytes. Surface immunologic markers did not differ between CD and HD MSC, with the only exception of sizeable levels of HLA-DR at early culture passages [12-

84% at passage (P)1] in the former. CD MSC ceased their growth at variable passages (from P8 to P25) and entered senescence without any change in morphology/proliferation rate. Array-comparative genomic hybridization demonstrated that CD MSC do not show imbalanced chromosomal rearrangements. Both CD and HD MSC inhibited in vitro proliferation of lymphocytes to mitogens. CD MSC show biologic characteristics similar to HD MSC and can be considered for anti-inflammatory and reparative cell therapy approaches in patients with refractory disease. Bernardo et al., "Phenotypical/functional characterization of in vitro-expanded mesenchymal stromal cells from patients with Crohn's disease" *Cytotherapy* 11(7):825-836 (2009).

Symptoms depend on what part of the gastrointestinal tract is affected. Symptoms range from mild to severe, and can come and go with periods of flare-ups. The main symptoms of Crohn's disease include, but are not limited to, crampy abdominal pain, fever, fatigue, loss of appetite, pain with passing stool (tenesmus), persistent, watery diarrhea, unexplained weight loss, constipation, eye inflammation, rectal fistulas, joint pain and swelling, mouth ulcers, rectal bleeding and bloody stools, skin lumps or sores (ulcers) and/or swollen gums.

I. Ulcerative Colitis

Ulcerative colitis is a type of inflammatory bowel disease (IBD) that affects the lining of the large intestine (colon) and rectum. The cause of ulcerative colitis is unknown but is believed to be an autoimmune disease. Najafi et al., "Autoimmunity in inflammatory bowel disease: a case of ulcerative colitis with diabetes mellitus, autoimmune hepatitis and autoimmune hypothyroidism" Turk J Pediatr. 2012 54(6):651-653. Ulcerative colitis may affect any age group, although there are peaks at ages 15-30 and then again at ages 50-70. The disease can begin the rectal area, and may involve the entire large intestine over time. It may also start in the rectum and other parts of the large intestine at the same time.

Mesenchymal stem cells (MSCs) are attractive cell sources in regenerative medicine. One study examined the effects of topical MSCs implantation on an experimental model of inflammatory bowel disease. Putative MSCs, isolated from bone marrow aspirates of male rats by dish adherence and expanded in vitro, were characterized by flow cytometry, reverse transcription-polymerase chain reaction, enzyme-linked immunosorbent assay, and differentiation assays. Experimental colitis was induced by intraluminal instillation of 2,4,6-trinitrobonzene sulfonic acid (TNBS) in the colons of male rats. The putative MSCs and unselected fresh bone marrow cells were injected into the colonic submucosa surrounding the area exposed to TNBS. The healing process of the injury was examined macroscopically and immunohistologically. Multipotent MSCs positive for CD29 and CD90, and negative for CD31 and CD34, were implanted into colon tissue surrounding the lesion; a majority of the engrafted cells were positive for vimentin. The implantation significantly accelerated healing of the damaged mucosa compared with vehicle-injected controls. The MSCs expressed vascular endothelial growth factor (VEGF) and transforming growth factor (TGF)-beta1 in vitro and after the implantation. The MSCs were successfully topically implanted in the colon and that they were associated with accelerated healing of TNBS-induced colitis. The beneficial effects of the MSCs might be mediated, at least in part, by their ability to differentiate into colonic interstitial cells and by their ability to provide VEGF and TGF-beta 1 to the injured area. Hayashi et al., "Topical implantation of mesenchymal stem cells has beneficial effects on healing of experimental colitis in rats" *J Pharmacol Exp Ther.* 326(2): 523-531 (2008).

Ulcerative colitis symptoms vary in severity and may start slowly or suddenly. About half of people only have mild symptoms. Others have more severe attacks that occur more often. Many factors can lead to attacks, including respiratory infections or physical stress. Usual symptoms may include, but are not limited to, abdominal pain and cramping, abdominal sounds (a gurgling or splashing sound heard over the intestine), blood and pus in the stools, diarrhea, fever, tenesmus (rectal pain), unexplained weight loss, gastrointestinal bleeding, joint pain and swelling, mouth sores (ulcers), nausea and vomiting and/or skin lumps or ulcers.

J. Dermatomyositis

Dermatomyositis is a muscle disease characterized by inflammation and a skin rash. It is a type of inflammatory myopathy. Currently, the cause of dermatomyositis is unknown but it is generally believed that the condition may be due to a viral infection of the muscles or an autoimmune disease. Anyone can develop dermatomyositis, but it most commonly occurs in children age 5-15 and adults age 40-60. Women develop this condition more often than men do.

To assess the safety and clinical efficacy of allogeneic mesenchymal stem cell transplantation (MSCT) in a small-scale pilot study with 10 patients with drug-resistant polymyositis (PM) or dermatomyositis (DM) was reported. A single-arm trial involving 10 patients with DM/PM who were either refractory to standard treatment, or had severe systemic involvement. All patients consented and underwent allogeneic MSCT. Clinical and laboratory manifestations were compared before and after MSCT. Improvements were seen in serum creatine kinase (CK), CK-MB, patient global assessment by visual analogue scale and muscle strength by manual muscle test in all patients, as well as improvement in interstitial lung disease in selected patients. Improvement in chronic non-healing skin ulcers was noted in one patient. Clinical responses were also seen in patients undergoing a second MSCT for recurrence of disease. MSCT appears safe and effective in drug-resistant patients with DM/PM. Larger-scale studies including a control group receiving standard treatment are needed to assess the long-term efficacy of allogeneic MSCT in refractory patients with DM/PM. Wang et al., "Efficacy of allogeneic mesenchymal stem cell transplantation in patients with drug-resistant polymyositis and dermatomyositis" *Ann Rheum Dis.* 70(7):1285-1288 (2011).

Juvenile dermatomyositis (JDM) is a chronic inflammatory disorder of unknown aetiology that affects muscle and skin. One report evaluated stem cell transplants on two patients with severe progressive JDM who developed contractures and were wheelchair dependent despite therapy including methotrexate (MTX), steroids, immunoglobulins, cyclosporin A, and rituximab. On account of the refractory disease, autologous stem cell transplantation (ASCT) was performed using a CD3/CD19-depleted graft after immunoablative conditioning with fludarabine, cyclophosphamide, and anti-thymocyte globulin. ASCT induced an improvement and sustained remission of the disease in both patients. ASCT may provide a therapeutic option with low toxicity for patients with severe, refractory JDM. Holzer et al., "Successful autologous stem cell transplantation in two patients with juvenile dermatomyositis" *Scand J Rheumatol.* 39(1):88-92 (2010).

Symptoms of dermatomyositis may include, but are not limited to, difficulty swallowing, muscle weakness, muscle stiffness, muscle soreness, purple/violent upper eyelids, purple/red skin rash and/or shortness of breath. The muscle weakness may appear suddenly or develop slowly over weeks or months. Difficulty may be encountered when the arms are raised over the head, rising from a sitting position and/or climbing stairs. The skin rash may appear over the face, knuckles, neck, shoulders, upper chest, and back.

V. Pharmaceutical Formulations

The present invention further provides pharmaceutical formulations. In one embodiment, the pharmaceutical formulations comprise a compound-loaded microparticle as described herein (e.g., a chemokine-loaded alginate microparticle).

In one embodiment, the pharmaceutical formulation is a compound-loaded microparticle population. In one embodiment, the compound-loaded microparticle population comprises a solid shape. In one embodiment, the solid shape of the compound-loaded microparticle population may include, but is not limited to, transdermal patches, ointments, lotions, creams, gels, suppositories, and powders. In one embodiment, the solid shape of the compound-loaded microparticle population may include, but is not limited to, powders or granules, suspensions or solutions in water or non-aqueous media, capsules, sachets and/or tablets The pharmaceutical formulations and/or compositions of the present invention may be administered in a number of ways depending upon whether local or systemic treatment is desired and upon the area to be treated.

Administration may be topical (including, but not limited to, ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Local administration may also be topical, but includes as well, intrarticular injection into synovial spaces of the body (i.e., for example, into articulating bone joints and/or cartilage). Parenteral administration includes, but is not limited to, intravenous, intraarterial, subcutaneous, intraperitoneal or intramuscular injection or infusion; or intracranial, e.g., intrathecal or intraventricular, administration.

Pharmaceutical compositions and formulations for topical administration may include, but are not limited to, transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also, be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product.

The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. The administering physician can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models or based on the examples described herein. In general, dosage is from 0.01 µg to 100 g per kg of body weight, and may be given once or more daily, weekly, monthly or yearly. The treating physician can estimate repetition rates for dosing based on measured residence times and concentrations of the drug in bodily fluids or tissues. Following successful treatment, it may be desirable to have the subject undergo maintenance therapy to prevent the recurrence of the disease state, wherein the compound is administered in maintenance doses, ranging from 0.01 µg to 100 g per kg of body weight, once or more daily, to once every 20 years.

VI. Compound Delivery Systems

In one embodiment, the present invention contemplates a compound-loaded microparticle delivery system that provides for a roughly uniform compound distribution and has controllable rates of compound release. However, it is not intended that a compound delivery system capable of creating chemokine gradients be limited to microparticles. For example, a variety of different media are described below that are useful in creating alternative compound delivery systems. It is also not intended that any one medium or carrier is limiting to the present invention. Note that any medium or carrier may be combined with another medium or carrier; for example, in one embodiment a polymer microparticle carrier attached to a compound may be combined with a gel medium.

Carriers or mediums for drug delivery systems contemplated by this invention may comprise a material including, but not limited to, gelatin, collagen, cellulose esters, dextran sulfate, pentosan polysulfate, chitin, saccharides, albumin, fibrin sealants, synthetic polyvinyl pyrrolidone, polyethylene oxide, polypropylene oxide, block polymers of polyethylene oxide and polypropylene oxide, polyethylene glycol, acrylates, acrylamides, methacrylates including, but not limited to, 2-hydroxyethyl methacrylate, poly(ortho esters), cyanoacrylates, gelatin-resorcin-aldehyde type bioadhesives, polyacrylic acid and copolymers and block copolymers thereof.

A. Microparticles

One embodiment of the present invention contemplates a medium comprising a microparticle. In one embodiment, the microparticle comprises alginate. In one embodiment, the alginate concentration may range from approximately 0.1-10% (w/w) of the microparticle. Preferably, microparticles include, but are not limited to, nanoparticles, microspheres, nanospheres, microcapsules, and/or nanocapsules. Preferably, some microparticles contemplated by the present invention comprise alginate, poly(lactide-co-glycolide), aliphatic polyesters including, but not limited to, poly-glycolic acid and poly-lactic acid, hyaluronic acid, modified polysacchrides, chitosan, cellulose, dextran, polyurethanes, polyacrylic acids, psuedo-poly(amino acids), polyhydroxybutrate-related copolymers, polyanhydrides, polymethylmethacrylate, poly(ethylene oxide), lecithin and phospholipids.

In one embodiment, the present invention contemplates a microparticle comprising a gelatin, or other polymeric cation having a similar charge density to gelatin (i.e., poly-L-lysine) and is used as a complex to form a primary microparticle. A primary microparticle is produced as a mixture of the following composition: i) Gelatin (60 bloom, type A from porcine skin), ii) chondroitin 4-sulfate (0.005%-0.1%), iii) glutaraldehyde (25%, grade 1), and iv) 1-ethyl-3-(3-dimethylaminopropyl)-carbodiimide hydrochloride (EDC hydrochloride), and ultra-pure sucrose (Sigma Chemical Co., St. Louis, Mo.). The source of gelatin is not thought to be critical; it can be from bovine, porcine, human, or other animal source. Typically, the polymeric cation is between 19,000-30,000 daltons. Chondroitin sulfate is then added to the complex with sodium sulfate, or ethanol as a coacervation agent.

Following the formation of a microparticle, a compound may be: i) directly bound to the surface of the microparticle; ii) indirectly attached using a "bridge" or "spacer"; or iii) encapsulated into the microparticle's void spaces. The amino groups of the gelatin lysine groups are easily derivatized to provide sites for direct coupling of a compound. Alternatively, spacers (i.e., linking molecules and derivatizing moieties on targeting ligands) such as avidin-biotin are also useful to indirectly couple targeting ligands to the microparticles. Stability of a microparticle can be controlled by the amount of glutaraldehyde-spacer crosslinking induced by the EDC hydrochloride. A controlled release medium is also empirically determined by the final density of glutaraldehyde-spacer crosslinks.

In one embodiment, the present invention contemplates microparticles formed by spray-drying a composition comprising fibrinogen or thrombin with a therapeutic agent. Preferably, these microparticles are soluble and the selected protein (i.e., fibrinogen or thrombin) creates the walls of the microparticles. Consequently, the therapeutic agents are incorporated within, and between, the protein walls of the microparticle. Heath et al., Microparticles And Their Use In Wound Therapy. U.S. Pat. No. 6,113,948 (herein incorporated by reference). Following the application of the microparticles to living tissue, the subsequent reaction between the fibrinogen and thrombin creates a tissue sealant thereby releasing the incorporated compound into the immediate surrounding area.

B. Liposomes

In one embodiment, the present invention contemplates liposomes comprising a population of microparticles. In one embodiment, the liposome further comprises a targeting ligand to a specific anatomical site. For example, surface functionalization of microparticles facilitation the construction highly specific functionalities that can be used as attachment points for a diverse range of targeting ligands such as antibodies, peptides, carbohydrates and/or vitamins. In recent years, an increasing number of studies have been devoted to the development of drug delivery systems and drug targeting. First attempts in this direction were accomplished using monoclonal antibodies or antibody fragments coupled with active compounds, such as antitumor drugs. This approach was made more efficient by the entrapment of drugs into liposomes. These colloidal systems have proved to be versatile carriers for a wide variety of i.v. administered active molecules. Their main advantage is that they offer a suitable means for delivering drugs combined with the potential of improving the therapeutic index while greatly reducing the side effects. Nobs et al., "Current Methods for Attaching Targeting Ligands to Liposomes and Nanoparticles" *J. Pharm. Sci.* 93:8, 1980-1992 (2004).

Two methods are generally used for attaching ligands to the liposomal surface: covalent and noncovalent coupling. For example, ligands may be bound to the surface of liposomes through hydrophobic anchors having functional groups. Long-chain fatty acid such as palmitic acid and phospholipids, such as phosphatidylethanolamine (PE) and phosphatidylinositol (PI) have been successfully used as anchors. Hughes et al., "Monoclonal antibody targeting of liposomes to mouse lung in vivo" *Cancer Res* 49:6214-6220 (1989); Huang et al., "Monoclonal antibody covalently coupled with fatty acid" *J Biol Chem* 255:8015-8018 (1980); Harsch et al., "Targeting of monoclonal antibody-coated liposomes to sheep red blood cells" *Biochem Biophys Res Commun* 103:1069-1076 (1981); Shen et al. "An improved method for covalent attachment of antibody to liposomes" *Biochim Biophys Acta* 689:31-37 (1982); Carpenter-Green et al., "Incorporation of acylated wheat germ agglutinin into liposomes" *Anal Biochem* 135:151-155 (1983); Weissig et al., "A new hydrophobic anchor for the attachment of proteins to liposomal membranes" *FEBS Len* 202:86-90 (1986); and Torchilin et al., "Phosphatidylinositol may serve as the hydrophobic anchor for immobilization of proteins on liposome surface" *FEBS Lett* 138:117-120 (1982). These anchors are incorporated into the liposomal membrane during the formation of liposomes.

There are essentially two approaches to covalently attach a targeting ligand to an anchor. A reaction first conjugates a targeting ligand and an anchor wherein the ligand/anchor complex is mixed with the other constituents of the liposome. Alternatively, an anchor may already be inserted into a liposome bilayer and the coupling reaction occurs on the surface of preformed liposomes. Torchilin et al., "Incorporation of hydrophilic protein modified with hydrophobic agent into liposome membrane" *Biochini Biophys Acta* 602:511-521 (1980). Among the hydrophobic anchors, PE is frequently used because it can be easily derivatized to offer functional groups.

For example, the coupling of targeting ligands to a liposome surface may involve thioether bonds wherein a reaction between thiol functions and (for example) maleimide groups is a highly efficient reaction that gives a stable thioether bond. Native thiol groups are present in some proteins, but in many others, thiol functions are either absent or present in insufficient amounts. Thus, they have to be added either via heterobifunctional crosslinking agents or be obtained by reducing existing disulfide bonds. Crosasso et al., "Antitumoral activity of liposomes and immunoliposomes containing 5-fluorouridine prodrugs" *J Pharm Sci* 86:832-839 (1997); and Derksen et al., "An improved method for the covalent coupling of proteins to liposomes" *Biochim Biophys Acta* 814:151-155 (1985).

Immunoliposome technology can be combined with sterically stabilized liposomes technology to give long circulating vesicles capable of selectively delivering compounds to target cells. There are two ways of obtaining this type of liposome: (1) antibodies are bound to the surface of liposome in parallel with PEG or (2) antibodies are linked to the distal end of PEG chains. For both approaches, PEG is incorporated into the bilayer membrane via an anchor such as distearoylphosphatidylethanolamine (DSPE). Koning et al., "Selective transfer of a lipophilic prodrug of 5-fluorodeoxyuridine from immunoliposomes to colon cancer cells" *Biochim Biophys Acta* 1420:153-167 (1999); Park et al., "Anti-HER2 immunoliposomes for targeted therapy of human tumors" *Cancer Lett* 118:153-160 (1997); Park et al., "Anti-HER2 immunoliposomes: Enhanced efficacy attributable to targeted delivery" *Clin Cancer Res* 8:1172-1181 (2002); Kirpotin et al., "Sterically stabilized anti-HER2 immunoliposomes: Design and targeting to human breast cancer cells in vitro" *Biochemistry* 36:66-75 (1997); and Hansen et al., "Attachment of antibodies to sterically stabilized liposomes: Evaluation, comparison and optimization of coupling procedures" *Biochim Biophys Acta* 1239:133-144 (1995).

Targeting ligands can also be attached to the surface of liposomes by an amide bond using an anchor functionalized with carboxylic acid end groups. For this purpose, distearoyl-N-(3-carboxypropionoyl poly(ethylene glycol)succinyl)phosphatidylethanolamine (DSPE-PEG-COOH), which offers carboxylic acid groups at the distant end of surface-grafted PEG chains is commonly used. Ishida et al., 2001. "Liposomes bearing polyethyleneglycol-coupled transferrin with intracellular targeting property to the solid tumors in vivo" *Pharm Res* 18:1042-1048 (2001); and Maruyama et al., "Targetability of novel immunoliposomes modified with amphipathic poly(ethylene glycol)s conjugated at their distal terminals to monoclonal antibodies" *Biochim Biophys Acta* 1234:74-80 (1995). The major advantage of this method is that no prior ligand modification is required, thus reducing the risk of denaturation and loss of its specific activity.

Antibodies can also be covalently bound to a liposome through their carbohydrate moieties to hydrazide groups grafted onto the liposomal surface to form a hydrazide bond. A mild oxidation of the carbohydrate groups on the constant region of the heavy chain of the immunoglobulin can produce aldehyde groups. The aldehyde groups then react with hydrazide groups of the anchor and/or the carbohydrate groups are oxidized either by galactose oxidase or by sodium periodate. Chua et al., 1984. "Attachment of immunoglobulin to liposomal membrane via protein carbohydrate" *Biochini Biophys Acta* 800:291-300 (1984); Harding et al., "Immunogenicity and pharmacokinetic attributes of poly(ethylene glycol)-grafted immunoliposomes" *Biochim Biophys Acta* 1327:181-192 (1997); Goren et al., "Targeting of stealth liposomes to erbB-2 (Her/2) receptor: In vitro and in vivo studies" *Br J Cancer* 74: 17491756 (1996); Lopes de Menezes et al., "In vitro and in vivo targeting of immunoliposomal doxorubicin to human B-cell lymphoma" *Cancer Res* 58: 3320-3330 (1998).

The avidin-biotin strategy has become an extremely useful and versatile tool for active targeting, especially owing to the possibility of applying it in a multistep approach. Magnani et al., "Quantitative comparison of direct antibody labeling and tumor pretargeting in uveal melanoma" *J Nucleic Med* 37: 967-971 (1996); Casalini et al., "Tumor pretargeting: Role of avidin/streptavidin on monoclonal antibody internalization" *J Nucleic Med* 38: 13781381 (1997); and Moro et al., "Tumor cell targeting with antibody-avidin complexes and biotinylated tumor necrosis factor al" *Cancer Res* 57: 1922-1928 (1997). The avidin-biotin technology has also been used in the field of liposomes. Loughrey et al., "A noncovalent method of attaching antibodies to liposomes" *Biochim Biophys Acta* 901: 157-160 (1987). Furthermore, biotinylated antibodies can be easily obtained. Mao S Y., "Biotinylation of antibodies" *Methods Mol Biol* 34: 49-52 (1994); Portnoy et al., "Monoclonal antibody-based assay for Alt al, a major Alternaria allergen" *Ann. Allergy Asthma Immunol* 81: 59-64 (1998); and Pieri et al., 1991. "Biotinylated basic fibroblast growth factor is biologically active" *Anal Biochem* 195: 214-219 (1991).

Liposomes are microscopic spherical lipid bilayers surrounding an aqueous core that are made from amphiphilic molecules such as phospholipids. For example, a liposome may trap a microparticle population between the hydrophobic tails of the phospholipid micelle, within in the liposome core and/or within in the liposome shell-like bilayer.

Liposomes have a special characteristic in that they enable water soluble and water insoluble chemicals to be used together in a medium without the use of surfactants or other emulsifiers. Liposomes can form spontaneously by forcefully mixing phosopholipids in aqueous media. Water soluble compounds are dissolved in an aqueous solution capable of hydrating phospholipids. Upon formation of the liposomes, therefore, these compounds are trapped within the aqueous liposomal center. The liposome wall, being a phospholipid membrane, holds fat soluble materials such as oils. Liposomes provide controlled release of incorporated compounds. In addition, liposomes can be coated with water soluble polymers, such as polyethylene glycol to increase the pharmacokinetic half-life.

In some embodiments, the present invention contemplates cationic and anionic liposomes, as well as liposomes having neutral lipids. Preferably, cationic liposomes comprise negatively-charged materials by mixing the materials and fatty acid liposomal components and allowing them to charge-associate. Clearly, the choice of a cationic or anionic liposome depends upon the desired pH of the final liposome mixture. Examples of cationic liposomes include lipofectin, lipofectamine, and lipofectace.

One embodiment of the present invention contemplates a medium comprising liposomes that provide controlled release of at least one microparticle population. Preferably, liposomes that are capable of controlled release: i) are biodegradable and non-toxic; ii) carry both water and oil soluble compounds; iii) solubilize recalcitrant compounds; iv) prevent compound oxidation; v) promote protein stabilization; vi) control hydration; vii) control compound release by variations in bilayer composition such as, but not limited to, fatty acid chain length, fatty acid lipid composition, relative amounts of saturated and unsaturated fatty acids, and physical configuration; viii) have solvent dependency; iv) have pH-dependency and v) have temperature dependency.

The compositions of liposomes are broadly categorized into two classifications. Conventional liposomes are generally mixtures of stabilized natural lecithin (PC) that may comprise synthetic identical-chain phospholipids that may or may not contain glycolipids. Special liposomes may comprise: i) bipolar fatty acids; ii) the ability to attach antibodies for tissue-targeted therapies; iii) coated with materials such as, but not limited to lipoprotein and carbohydrate; iv) multiple encapsulation and v) emulsion compatibility.

Liposomes may be easily made in the laboratory by methods such as, but not limited to, sonication and vibration. Alternatively, compound-delivery liposomes are commercially available. For example, Collaborative Laboratories, Inc. are known to manufacture custom designed liposomes for specific delivery requirements.

C. Microspheres And Microcapsules

Microspheres and microcapsules are alternatives to microparticles and are useful due to their ability to maintain a generally uniform distribution, provide stable controlled compound release and are economical to produce and dispense. Preferably, an associated delivery gel or the compound-impregnated gel is clear or, alternatively, said gel is colored for easy visualization by medical personnel.

Microspheres are obtainable commercially (Protease®, Alkerme's: Cambridge, Mass.). For example, a freeze dried medium comprising at least one therapeutic agent is homogenized in a suitable solvent and sprayed to manufacture microspheres in the range of 20 to 90 µm. Techniques are then followed that maintain sustained release integrity during phases of purification, encapsulation and storage. Scott et al., Improving Protein Therapeutics With Sustained Release Formulations, Nature Biotechnology, Volume 16:153-157 (1998).

Modification of the microsphere composition by the use of biodegradable polymers can provide an ability to control the rate of therapeutic agent release. Miller et al., Degradation Rates of Oral Resorbable Implants {Polylactates and Polyglycolates: Rate Modification and Changes in PLA/PGA Copolymer Ratios, J. Biomed. Mater. Res., Vol. 11:711-719 (1977).

Alternatively, a sustained or controlled release microsphere preparation is prepared using an in-water drying method, where an organic solvent solution of a biodegradable polymer metal salt is first prepared. Subsequently, a dissolved or dispersed medium of a compound is added to the biodegradable polymer metal salt solution. The weight ratio of a therapeutic agent to the biodegradable polymer metal salt may for example be about 1:100000 to about 1:1, preferably about 1:20000 to about 1:500 and more preferably about 1:10000 to about 1:500. Next, the organic solvent solution containing the biodegradable polymer metal salt and therapeutic agent is poured into an aqueous phase to prepare an oil/water emulsion. The solvent in the oil phase is then evaporated off to provide microspheres. Finally, these microspheres are then recovered, washed and lyophilized. Thereafter, the microspheres may be heated under reduced pressure to remove the residual water and organic solvent.

Other methods useful in producing microspheres that are compatible with a biodegradable polymer metal salt and therapeutic agent mixture are: i) phase separation during a gradual addition of a coacervating agent; ii) an in-water drying method or phase separation method, where an antiflocculant is added to prevent particle agglomeration and iii) by a spray-drying method.

In one embodiment, the present invention contemplates a medium comprising a microsphere or microcapsule capable of delivering a controlled release of a compound for a duration of approximately between 1 day and 6 months. In one embodiment, the microsphere or microparticle may be colored to allow the medical practitioner the ability to see the medium clearly as it is dispensed. In another embodiment, the microsphere or microcapsule may be clear. In another embodiment, the microsphere or microparticle is impregnated with a radio-opaque fluoroscopic dye.

Controlled release microcapsules may be produced by using known encapsulation techniques such as centrifugal extrusion, pan coating and air suspension. Such microspheres and/or microcapsules can be engineered to achieve desired release rates. For example, Oliosphere® (Macromed) is a controlled release microsphere system. These particular microsphere's are available in uniform sizes ranging between 5-500 µm and composed of biocompatible and biodegradable polymers. Specific polymer compositions of a microsphere can control the therapeutic agent release rate such that custom-designed microspheres are possible, including effective management of the burst effect. ProMaxx® (Epic Therapeutics, Inc.) is a protein-matrix delivery system. The system is aqueous in nature and is adaptable to standard pharmaceutical delivery models. In particular, ProMaxx® are bioerodible protein microspheres that deliver both small and macromolecular drugs, and may be customized regarding both microsphere size and desired release characteristics.

In one embodiment, a microsphere or microparticle comprises a pH sensitive encapsulation material that is stable at a pH less than the pH of the internal mesentery. The typical range in the internal mesentery is pH 7.6 to pH 7.2. Consequently, the microcapsules should be maintained at a pH of less than 7. However, if pH variability is expected, the pH sensitive material can be selected based on the different pH criteria needed for the dissolution of the microcapsules. The encapsulated compound, therefore, will be selected for the pH environment in which dissolution is desired and stored in a pH preselected to maintain stability. Examples of pH sensitive material useful as encapsulants are Eudragit® L-100 or S-100 (Rohm GMBH), hydroxypropyl methylcellulose phthalate, hydroxypropyl methylcellulose acetate succinate, polyvinyl acetate phthalate, cellulose acetate phthalate, and cellulose acetate trimellitate. In one embodiment, lipids comprise the inner coating of the microcapsules. In these compositions, these lipids may be, but are not limited to, partial esters of fatty acids and hexitiol anhydrides, and edible fats such as triglycerides. Lew C. W., Controlled-Release pH Sensitive Capsule And Adhesive System And Method. U.S. Pat. No. 5,364,634 (herein incorporated by reference).

One having skill in the art will understand that the shape of the microspheres need not be exactly spherical; only as very small particles capable of being sprayed or spread into or onto a surgical site (i.e., either open or closed). In one embodiment, microparticles are comprised of a biocompatible and/or biodegradable material selected from the group consisting of polylactide, polyglycolide and copolymers of lactide/glycolide (PLGA), hyaluronic acid, modified polysaccharides and any other well-known material.

VII. Antibodies

In one embodiment, the present invention contemplates a targeting ligand comprising an antibodies (i.e., for example, polyclonal or monoclonal). In one embodiment, the present invention provides monoclonal antibodies that specifically bind to a liposomal anchor. Although it is not necessary to understand the mechanism of an invention it is believed that such targeting ligands facilitate the aggregation of liposomes comprising alginate microparticles of the present invention at a specific anatomical site and/or tissue. It is further believed that such anatomical sites and/or tissues comprise epitopes having specific affinity for the targeting ligands.

An antibody against a protein of the present invention may be any monoclonal or polyclonal antibody, as long as it can recognize (e.g., has specific affinity) a protein. Antibodies can be produced by using a protein of the present invention as the antigen according to a conventional antibody or antiserum preparation process.

The present invention contemplates the use of both monoclonal and polyclonal antibodies. Any suitable method may be used to generate the antibodies used in the methods and compositions of the present invention, including but not limited to, those disclosed herein. For example, for preparation of a monoclonal antibody, protein, as such, or together with a suitable carrier or diluent is administered to an animal (e.g., a mammal) under conditions that permit the production of antibodies. For enhancing the antibody production capability, complete or incomplete Freund's adjuvant may be administered. Normally, the protein is administered once every 2 weeks to 6 weeks, in total, about 2 times to about 10 times. Animals suitable for use in such methods include, but are not limited to, primates, rabbits, dogs, guinea pigs, mice, rats, sheep, goats, etc.

For preparing monoclonal antibody-producing cells, an individual animal whose antibody titer has been confirmed (e.g., a mouse) is selected, and 2 days to 5 days after the final immunization, its spleen or lymph node is harvested and antibody-producing cells contained therein are fused with myeloma cells to prepare the desired monoclonal antibody producer hybridoma. Measurement of the antibody titer in antiserum can be carried out, for example, by reacting the labeled protein, as described hereinafter and antiserum and then measuring the activity of the labeling agent bound to the antibody. The cell fusion can be carried out according to known methods, for example, the method described by Koehler and Milstein (Nature 256:495 [1975]). As a fusion promoter, for example, polyethylene glycol (PEG) or Sendai virus (HVJ), preferably PEG is used.

Examples of myeloma cells include NS-1, P3U1, SP2/0, AP-1 and the like. The proportion of the number of antibody producer cells (spleen cells) and the number of myeloma cells to be used is preferably about 1:1 to about 20:1. PEG (preferably PEG 1000-PEG 6000) is preferably added in concentration of about 10% to about 80%. Cell fusion can be carried out efficiently by incubating a mixture of both cells at about 20° C. to about 40° C., preferably about 30° C. to about 37° C. for about 1 minute to 10 minutes.

Various methods may be used for screening for a hybridoma producing the antibody (e.g., against a tumor antigen or autoantibody of the present invention). For example, where a supernatant of the hybridoma is added to a solid phase (e.g., microplate) to which antibody is adsorbed directly or together with a carrier and then an anti-immunoglobulin antibody (if mouse cells are used in cell fusion, anti-mouse immunoglobulin antibody is used) or Protein A labeled with a radioactive substance or an enzyme is added to detect the monoclonal antibody against the protein bound to the solid phase. Alternately, a supernatant of the hybridoma is added to a solid phase to which an anti-immunoglobulin antibody or Protein A is adsorbed and then the protein labeled with a radioactive substance or an enzyme is added to detect the monoclonal antibody against the protein bound to the solid phase.

Selection of the monoclonal antibody can be carried out according to any known method or its modification. Normally, a medium for animal cells to which HAT (hypoxanthine, aminopterin, thymidine) are added is employed. Any selection and growth medium can be employed as long as the hybridoma can grow. For example, RPMI 1640 medium containing 1% to 20%, preferably 10% to 20% fetal bovine serum, GIT medium containing 1% to 10% fetal bovine serum, a serum free medium for cultivation of a hybridoma (SFM-101, Nissui Seiyaku) and the like can be used. Normally, the cultivation is carried out at 20° C. to 40° C., preferably 37° C. for about 5 days to 3 weeks, preferably 1 week to 2 weeks under about 5% CO2 gas. The antibody titer of the supernatant of a hybridoma culture can be measured according to the same manner as described above with respect to the antibody titer of the anti-protein in the antiserum. Separation and purification of a monoclonal antibody can be carried out according to the same manner as those of conventional polyclonal antibodies such as separation and purification of immunoglobulins, for example, salting-out, alcoholic precipitation, isoelectric point precipitation, electrophoresis, adsorption and desorption with ion exchangers (e.g., DEAE), ultracentrifugation, gel filtration, or a specific purification method wherein only an antibody is collected with an active adsorbent such as an antigen-binding solid phase, Protein A or Protein G and dissociating the binding to obtain the antibody.

Polyclonal antibodies may be prepared by any known method or modifications of these methods including obtaining antibodies from patients. For example, a complex of an immunogen (an antigen against the protein) and a carrier protein is prepared and an animal is immunized by the complex according to the same manner as that described with respect to the above monoclonal antibody preparation. A material containing the antibody against is recovered from the immunized animal and the antibody is separated and purified.

As to the complex of the immunogen and the carrier protein to be used for immunization of an animal, any carrier protein and any mixing proportion of the carrier and a hapten can be employed as long as an antibody against the hapten, which is crosslinked on the carrier and used for immunization, is produced efficiently. For example, bovine serum albumin, bovine cycloglobulin, keyhole limpet hemocyanin, etc. may be coupled to an hapten in a weight ratio of about 0.1 part to about 20 parts, preferably, about 1 part to about 5 parts per 1 part of the hapten. In addition, various condensing agents can be used for coupling of a hapten and a carrier. For example, glutaraldehyde, carbodiimide, maleimide activated ester, activated ester reagents containing thiol group or dithiopyridyl group, and the like find use with the present invention. The condensation product as such or together with a suitable carrier or diluent is administered to a site of an animal that permits the antibody production. For enhancing the antibody production capability, complete or incomplete Freund's adjuvant may be administered. Normally, the protein is administered once every 2 weeks to 6 weeks, in total, about 3 times to about 10 times. The polyclonal antibody is recovered from blood, ascites and the like, of an animal immunized by the above method. The antibody titer in the antiserum can be measured according to the same manner as that described above with respect to the supernatant of the hybridoma culture. Separation and purification of the antibody can be carried out according to the same separation and purification method of immunoglobulin as that described with respect to the above monoclonal antibody.

The protein used herein as the immunogen is not limited to any particular type of immunogen. For example, a protein expressed resulting from a virus infection (further including a gene having a nucleotide sequence partly altered) can be used as the immunogen. Further, fragments of the protein may be used. Fragments may be obtained by any methods including, but not limited to expressing a fragment of the gene, enzymatic processing of the protein, chemical synthesis, and the like.

EXPERIMENTAL

Example I

MSC Migration to an Arthritic Injury

This example describes a mouse "sports injury" model that could be used to induce articular joint damage analogous to many human joint conditions including, but not limited to, injury-induced arthritis, rheumatoid arthritis and/or osteoarthritis.

Under brief anesthesia, mice are injected intra-articularly with mono-iodoacetate (MIA)(Sigma-Aldrich, USA) dissolved in 25 μl of saline, or with only 25 μl of saline (controls). The syringe is inserted through the patellar ligament into the intra-articular joint space of the left knee. Animals are randomly assigned to each group.

Subsequently, each mouse is injected with alginate PDGF microparticles and luciferin-MSCs. See, FIG. 4A. The MIA injection is shown to be responsible for the observed articular cartilage destruction because the injection of a blank microparticle population is shown not cause any damage. See, FIG. 4B. The lucifern loaded MSCs are then subjected to fluorescence tracking and localization of the injected microparticles to document their migration pattern. In particular, the MSCs are observed to migrate to the specific mouse leg joint injected with MIA. See, FIG. 4C.

Articular joints assessed after injection of blank microparticles showed no articular joint damage at either three (3) days after injection or twenty-one days after injection as compared to a physiological buffered saline (PBS) control injection. See, FIG. 5A-C.

Example II

In Vitro Degradation of Alginate Microparticles

This example demonstrates that the alginate microparticles contemplated by this invention degrade in a manner that correlates with the in vitro and in vivo chemokine release patterns.

Photomicrographs taken immediately after placement into the in vitro release system showed no degradation of the microparticles. See, FIGS. 6A and 6B. Photomicrographs demonstrated a physical erosion pattern after thirty (30) days that correlated with the observed PDGF release profiles. See, FIGS. 6C and 6D.

Example III

Cytotoxicity of Alginate Microparticles

This example demonstrates that the alginate microparticles contemplated by this invention are not cytotoxic to MSCs as determined in an in vitro co-incubation assay.

Alginate microparticles and MSCs were mixed together in a physiologically balanced buffer solution. Photomicrographs demonstrated a lack of cytotoxicity of the microparticles on the MSCs by demonstrating that MSCs observed in a bright field image co-localized with calcein stained MSCs. See, FIGS. 7A and 7B, respectively. The lack of non-viability was confirmed by the lack of red stain subsequent to ethidium heterodimer-1. See, FIG. 7C. The co-localization of bright field MSCs images with the calcein/ethidium hetereodimer-1 stain images is demonstrated by an overlay of the FIG. 7A-C photomicrographs. See, FIG. 7D.

Example IV

MSC Migration to an Inflammation Injury

This example assesses hMSCs migration in response to a PDGF gradient in an inflammatory environment as it would be expected in an osteoarthritic joint or in several of the other diseases as described herein. hMSCs have been harvested from the bone marrow of different human donors undergoing total hip replacement. The use of different donors of primary cells is intended to account for the known high degree of variability from individual to individual and to assess the effectiveness of hMSCs recruitment through PDGF gradients. To simulate the presence of an inflammatory condition, hMSCs have been exposed to IL1-β during culture and their migration towards a PDGF gradient is then assessed.

Example V

MSC Migration to a Human Joint

This example assesses hMSCs migration in response to a PDGF gradient within the tissues of a human joint. Preliminary data suggests that a PDGF gradient successfully recruits hMSCs once applied in vivo.

An osteochondral (bone+cartilage) model has been developed that reproduces in the lab a human knee joint. Specifically, osteochondral plugs of different dimensions (e.g., 8-20 mm) have been obtained from human arthroplasty samples from patients undergoing total knee replacement. See, FIG. 8. It is known that drilling may result in cell death. Live-dead assay was performed on cross sections of two osteochondral plugs. Specifically, the calcein stain (green) shows live cells, and an ethidium homodimer-1 stain (red) shows dead cells. Plugs drilled without saline irrigation exhibit massive cell death, as exhibited by the predominance of red stain versus green stain in tissue sample slices. See, FIG. 9A. Whereas minimal or no significant cell death is observed when cold saline irrigation is used during drilling, as exhibited by the predominance of green stain versus red stain in tissue sample slices. See, FIG. 9B. The application of cold saline irrigation during drilling retained good cell viability in both bone and cartilage.

Example VI

In Vivo Mouse MSC Migration

This example provides an experiment using mouse MSCs (mMSCs) migration towards a joint using live animal imaging and fluorescent or fluorescently tagged mMSCs.

Mouse MSCs are extracted from luciferase positive mice or from regular mice and then transfected to express a fluorescent molecule. Luciferase positive mice are preferable in that they offer easy access to fluorescent cells without the need for additional transfection and fluorescence maintains the same intensity also after cell proliferation.

PDGF releasing microparticles are injected in the right knee joint of a wild type mouse, whereas the left knee is injected with either blank microparticles or PBS for contralateral control. Alternatively to intrarticular injection, injection can occur in the tissue nearby the mouse knee joint as it allows for a higher injection volume. This can be justified in a mouse since the smaller dimensions allow only a very limited intrarticular injection volume (differently from humans or larger animals), but at the same time the distance between the intrarticular space and the nearby tissue is also smaller.

After allowing the joint to heal from the injection and the microparticles to start releasing, fluorescent mMSCs are injected in the mouse blood stream and their distribution within the body is monitored by live animal imaging to assess increased homing to the joint injected with PDGF microparticles. After sacrificing the mice, the joints are also analyze, for instance by immunohistochemistry, to assess the localization of the MSCs in the joint.

Example VII

In Vivo MSC Treatment of Inflammatory Joint Damage

This example provides an experiment treating local joint damage causing joint inflammation and tissue damage by induction and migration of MSCs that reduce the swelling and initiate repair of tissue damage.

Joint inflammation and damage in mice is experimentally caused using three different methods: a) direct injection of mono-iodoacetate in the joint; b) localized controlled injurious impact of the knee; c) collagen-induced arthritis (mice are immunized against collagen type II and start developing arthritis after 2-3 weeks). At different time points after the above treatments, right knee joints are injected with PDGF releasing microparticles and left knee joints are used as control with blank microparticles or PDGF injections. Inflammation over time is monitored by measuring joint swelling and assessing joint functionality. Mice are also sacrificed at specific time points and the tissues are analyzed, for instance by histology and immunohistochemistry, to assess the level of inflammation, the extension of tissue damage versus undamaged/repaired tissue, the presence of mMSCs as well as of immune cells such as macrophages, B cells and T cells.

Example VIII

Preparation of Alginate Microparticles

This example provides the basic protocol for making microparticle having any desired alginate concentration.

Reagents:
  De-ionized (DI) $H_2O$
  Medium Viscosity Alginate
  Hypromellose (HPMC)
  Calcium chloride ($CaCl_2$)
  Iso-Octane
  Span®80
  Tween®80
  2-propanol Preparation:
  1) Prepare 70 mL of 1.4 M $CaCl_2$ in DI $H_2O$
     a. ~14.4 g of $CaCl_2$
  2) Prepare 3% Alginate/HPMC (v/v) in DI $H_2O$ (Alginate:HPMC=9:1)=10 mL
     a. ~30 mg HPMC: 270 mg Alginate
        i. One of skill in the art would know how to adjust the alginate/HPMC ratio to achieve microparticle with higher and/or lower alginate concentrations.
     b. Place on magnetic stirring plate and allow to mix fully
     c. * Take note of how much was added for yield calculation*
  3) Prepare 30% (v/v) Tween® 80 in DI $H_2O$ (10 mL total)
     a. ~3 mL Tween® 80:7 mL DI $H_2O$
  4) Prepare 2.5% (v/v) Span® 80 in Iso-Octane (70 mL total) in a tall 200 mL beaker
     a. ~1.75 mL Span® 80:68.25 mL Iso-Octane
     b. *Prepare solution last, right before homogenizing step*

Procedure:
  1) Place the alginate/HPMC solution into two 5 mL syringes and remove as many bubbles as possible by placing syringes into desiccator. (1-2 hours)
     a. Take note of the volumes before and after desiccation for yield calculation
  2) Place beaker with Span® 80/Iso-Octane solution under homogenizer and set speed to 7500 rpm. Allow this to run for ~30 seconds before adding alginate/HPMC
  3) Slowly add alginate/HPMC solution (dropwise) into beaker
     a. Take note of how much was added
  4) Immediately add 1.25 mL of the 30% Tween® 80
  5) Allow mixing for 3 minutes
  6) Pipet 70 mL of $CaCl_2$, 10 mL at a time
  7) Allow mixing for 3 minutes
  8) Pipet 10 mL of 2-propanol to cure microparticles (MPs)
  9) Allow mixing for 3 minutes
  10) Pour solution in 3, 50 mL falcon tubes
  11) Spin at 2500 rpm for 1 minutes, collect all MPs in 1 tube
  12) Wash with 2-propanol 2 times
     a. wait 5 minutes in between washes to further cure MPs
  13) Wash with DI $H_2O$ 3 times
  14) Freeze MPs and then lyophilize for a day.

We claim:

1. A controlled release microparticle comprising
   a) a chemokine;
   b) alginate at a concentration from about 1% to about 4% v of alginate/v of the microparticle, and
   c) hypromellose (HPMC).

2. The microparticle of claim 1, wherein the chemokine is selected from the group consisting of transforming growth factor-alpha (TGFα), insulin-like growth factor 1 (IGF-1), insulin-like growth factor 2 (IGF-2), CXC motif chemokine 12 (CXCL12), C—C motif chemokine ligand 5 (CCL5), and C—C motif chemokine 22 (CCL22).

3. The microparticle of claim 1, wherein the alginate microparticle is biodegradable.

4. The microparticle of claim 1, wherein the chemokine is released to form a biomimetic gradient.

5. A method of treating an autoimmune disease in a subject in need thereof, comprising administering a controlled release microparticle comprising:
   a) a chemokine;
   b) alginate at a concentration from about 1% to about 4% v of alginate/v of the microparticle, and
   c) hypromellose (HPMC).

6. The method of claim 5, wherein the chemokine is selected from the group consisting of transforming growth factor-alpha (TGFα), insulin-like growth factor 1 (IGF-1), insulin-like growth factor 2 (IGF-2), CXC motif chemokine 12 (CXCL12), C—C motif chemokine ligand 5 (CCL5), and C—C motif chemokine 22 (CCL22).

7. The method of claim 5, wherein the chemokine induces migration of multipotent stem cells towards the microparticle.

8. The method of claim 5, wherein the chemokine is released from the microparticle to form a biomimetic gradient.

9. The method of claim 5, wherein the microparticle is encapsulated in a liposome.

10. The method of claim 5, wherein the administering is parental, topical, oral, or intracranial.

11. The method of claim 5, wherein the autoimmune disease is selected from the group consisting of type 1 diabetes, alopecia areata, systemic lupus erythematosus, Sjogren syndrome, rheumatoid arthritis, antiphospholipid antibody syndrome, multiple sclerosis, Crohn's disease, ulcerative colitis, and dermatomyositis.

12. The method of claim 5, wherein the subject is human.

* * * * *